(12) United States Patent
Rismani et al.

(10) Patent No.: US 11,572,394 B2
(45) Date of Patent: Feb. 7, 2023

(54) PEPTIDES FOR TARGETING LRP6-OVEREXPRESSED CELLS

(71) Applicants: Elham Rismani, Tehran (IR); Ladan TeimooriToolabi, Tehran (IR); Morteza Karimipoor, Tehran (IR); Seyed Shahriar Arab, Tehran (IR)

(72) Inventors: Elham Rismani, Tehran (IR); Ladan TeimooriToolabi, Tehran (IR); Morteza Karimipoor, Tehran (IR); Seyed Shahriar Arab, Tehran (IR)

(73) Assignees: PASTEUR INSTITUTE OF IRAN, Tehran (IR); ELHAM RISMANI, Tehran (IR); LADAN TEIMOORITOOLABI, Tehran (IR)

( * ) Notice: Subject to any disclaimer, the term of this patent is extended or adjusted under 35 U.S.C. 154(b) by 0 days.

(21) Appl. No.: 17/175,704

(22) Filed: Feb. 15, 2021

(65) Prior Publication Data
US 2021/0198329 A1 Jul. 1, 2021

Related U.S. Application Data

(60) Provisional application No. 62/977,291, filed on Feb. 16, 2020.

(51) Int. Cl.
| | | |
|---|---|---|
| *C07K 14/47* | (2006.01) | |
| *C07K 7/08* | (2006.01) | |
| *G01N 33/574* | (2006.01) | |
| *A61P 35/00* | (2006.01) | |
| *A61N 5/06* | (2006.01) | |
| *A61K 38/00* | (2006.01) | |
| *A61N 2/00* | (2006.01) | |

(52) U.S. Cl.
CPC ............. *C07K 14/47* (2013.01); *A61P 35/00* (2018.01); *C07K 7/08* (2013.01); *G01N 33/57492* (2013.01); *A61K 38/00* (2013.01); *A61N 2/002* (2013.01); *A61N 5/062* (2013.01); *A61N 5/0625* (2013.01)

(58) Field of Classification Search
None
See application file for complete search history.

(56) References Cited

FOREIGN PATENT DOCUMENTS

WO  WO 2008/116171  *  9/2008

* cited by examiner

*Primary Examiner* — Sergio Coffa
(74) *Attorney, Agent, or Firm* — Bajwa IP Law Firm; Haris Zaheer Bajwa

(57) ABSTRACT

A composition for targeting low-density lipoprotein receptor-related protein 6 (LRP6)-overexpressed cells. The composition includes a peptide including at least one of SEQ ID NO: 1 and SEQ ID NO: 3.

18 Claims, 37 Drawing Sheets

Specification includes a Sequence Listing.

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Synthetic sequence of  Peptide-1

<400> SEQUENCE: 1

Asn Ser Ser Ser Leu Ser Ser Gly Ser Gly Asn Asn Ala Asn Gly Asn
1               5                   10                  15

Phe Leu Thr Tyr Tyr
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic sequence of Peptide-2

<400> SEQUENCE: 2

Gln Val Cys Thr Lys His Arg Arg Lys Gly Ser His Gly Leu Glu Ile
1               5                   10                  15

Phe Gln Arg Cys Tyr
            20

<210> SEQ ID NO 3
```

```
<211> LENGTH: 19
<212> TYPE: PRT
<213> ORGANISM: Artificial Sequence
<220> FEATURE:
<223> OTHER INFORMATION: Synthetic sequence of Peptide-3

<400> SEQUENCE: 3

Asn Gly Tyr Ile Thr Phe Gln Asp Gly Asn Asp Tyr Phe Arg Phe Pro
1               5                   10                  15

Leu Asn Asn

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence of Peptide-4
<220> FEATURE:
<221> NAME/KEY: DISULFID
<222> LOCATION: (1)..(11)

<400> SEQUENCE: 4

Cys Cys Ala Arg His Phe Trp Ser Lys Ile Cys
1               5                   10
```

PEPTIDES FOR TARGETING LRP6-OVEREXPRESSED CELLS

CROSS-REFERENCE TO RELATED APPLICATION

This application claims the benefit of priority from U.S. Provisional Patent Application Ser. No. 62/977,291, filed on Feb. 16, 2020, and entitled "PEPTIDES FOR TARGETING LRP6 HAVING INHIBITORY EFFECTS AGAINST CANCER CELLS," which is incorporated herein by reference in its entirety.

TECHNICAL FIELD

The present disclosure generally relates to anticancer drugs, particularly to anticancer drugs for inhibiting proliferation of cancer cells, and more particularly to peptide-based anticancer drugs for inhibiting the Wnt signaling pathway in cancer cells.

BACKGROUND

Colorectal cancer is a major health problem with complex and varied pathogenesis in which the misregulation of different molecular pathways may be considered a significant factor involved in different phenotypes of colorectal cancer. One of the most common molecular pathways involved in various cancers including colon, stomach, and lung is the Wnt signaling pathway, which is highly active in about 85% of colon cancers, about 70% of recurrent colon cancers, more than 50% of breast cancers, and about 25% of melanoma cases. While regulation of the Wnt signaling pathway may occur at an extracellular level by expression and sequestration of antagonists, targeting specific receptors that show overexpression in tumors may be considered as an approach to inhibit the Wnt signaling pathway.

Genetic and biochemical studies have shown that low-density lipoprotein receptor-related protein 6 (LRP6) is an essential element in the Wnt signaling pathway and its overexpression in malignant cells causes tumorigenesis. Also, the presence of Dickkopf-related protein 1 (DKK1), as an antagonist ligand with a high affinity for the LRP6, is critical for inhibiting the Wnt signaling pathway. As a result, reduced expression of the DKK1 may lead to the progression of various cancers, such as colorectal, colon and rectal, melanoma, prostate, and breast cancer. Overactivation of the Wnt signaling pathway in cancer pathogenesis has led to a search for new DKK1-derived antagonists to inhibit the proliferation of LRP6-overexpressed cells and help cancer treatment.

Targeted therapeutic approaches have introduced inhibitors of the Wnt signaling pathway in human cancer, including natural compounds, small molecule inhibitors, virus-based inhibitors, and antibodies. However, peptide-based inhibitors have several advantages, such as small size, rapid synthesis, higher stability, and a simple and cost-effective production process over small molecules and antibodies. Moreover, the peptide-based inhibitors' chemical structure may be more consistent with their target proteins' chemical structure than proteins and small molecules.

Hence, there is a need for effective peptide-based inhibitors of the Wnt signaling pathway to target and kill cancerous cells that overexpress LRP6 on their surfaces. Also, there is a need for a method for detecting LRP6-overexpressed cells in biological samples. Moreover, there is a need for targeting the LRP6-overexpressed cells in a subject.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary composition for targeting low-density lipoprotein receptor-related protein 6 (LRP6)-overexpressed cells. In an exemplary embodiment, exemplary composition may include an exemplary peptide. In an exemplary embodiment, exemplary peptide may include at least one of SEQ ID NO: 1 and SEQ ID NO: 3. In an exemplary embodiment, exemplary composition may further include at least one of SEQ ID NO: 2 and SEQ ID NO: 4.

In an exemplary embodiment, exemplary composition may further include a tag conjugated to exemplary peptide. In an exemplary embodiment, the tag may include at least one of a therapeutic tag and a diagnostic tag. In an exemplary embodiment, the diagnostic tag may include at least one of a radioactive substance, a dye, a contrast agent, a fluorophore molecule, a nanoparticle, a bioluminescent molecule, an affinity agent, and a magnetic agent. In an exemplary embodiment, the therapeutic tag may include at least one of a chemotherapeutic drug, a toxin, an anticancer growth inhibitor compound, an anticancer siRNA, and an anticancer antagomir. In an exemplary embodiment, the chemotherapeutic drug may include at least one of cisplatin, paclitaxel, carboplatin, topotecan, 5-fluorouracil, mitomycin C, docetaxel, oxaliplatin, epirubicin, cyclophosphamide, methotrexate, doxorubicin, and irinotecan.

In an exemplary embodiment, the LRP6-overexpressed cells may include LRP6-overexpressed cells of at least one of colorectal cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, and bladder cancer. In an exemplary embodiment, exemplary peptide may have a binding affinity to LRP6 with a dissociation constant (Kd) between about 1 µM and about 1000 µM.

In another general aspect, the present disclosure describes an exemplary method for targeting LRP6-overexpressed cells in a subject. In an exemplary embodiment, exemplary method may include administering an effective amount of an exemplary composition to the subject. In an exemplary embodiment, exemplary peptide may include at least one of SEQ ID NO: 1 and SEQ ID NO: 3. In an exemplary embodiment, exemplary peptide may further include at least one of SEQ ID NO: 2 and SEQ ID NO: 4.

In an exemplary embodiment, the subject may include at least one of a human and an animal. In an exemplary embodiment, administering the effective amount of exemplary composition to the subject may include at least one of intravenous, intratumoral, intradermal, intramuscular, subcutaneous, rectal, and oral administration. In an exemplary embodiment, exemplary method may further include killing the LRP6-overexpressed cells in the subject by conducting at least one of magnetic hyperthermia, photodynamic therapy, and photothermal therapy.

In another general aspect, the present disclosure describes an exemplary method for detecting LRP6-overexpressed cells in a biological sample. In an exemplary embodiment, exemplary method may include putting the biological sample in contact with exemplary composition and determining the presence of an LRP6-overexpressed cell in the biological sample responsive to detecting exemplary peptide bound to the LRP6-overexpressed cell. In an exemplary embodiment, exemplary composition may include an exemplary peptide and a diagnostic tag conjugated to exemplary peptide. In an exemplary embodiment, exemplary peptide may include at least one of SEQ ID NO: 1 and SEQ ID NO: 3. In an exemplary embodiment, exemplary peptide may further include at least one of SEQ ID NO: 2 and SEQ ID NO: 4.

In an exemplary embodiment, detecting exemplary peptide bound to LRP6-overexpressed cell may include detecting exemplary peptide bound to the LRP6-overexpressed cell by conducting at least one of a chemiluminescent assay, an immunofluorescent assay, enzyme-linked immunosorbent assay (ELISA), radioimmunoassay, a Western blot assay, an enzyme immunoassay, an immunoprecipitation assay, an immunohistochemical assay, an immunochromatographic assay, a dot blot assay, a slot blot assay, confocal imaging, laser scanning microscopy, and flow cytometry. In an exemplary embodiment, putting the biological sample in contact with exemplary composition may include putting at least one of a blood sample, a plasma sample, a serum sample, a urine sample, a fecal sample, a cervix sample, and a semen sample in contact with exemplary composition.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
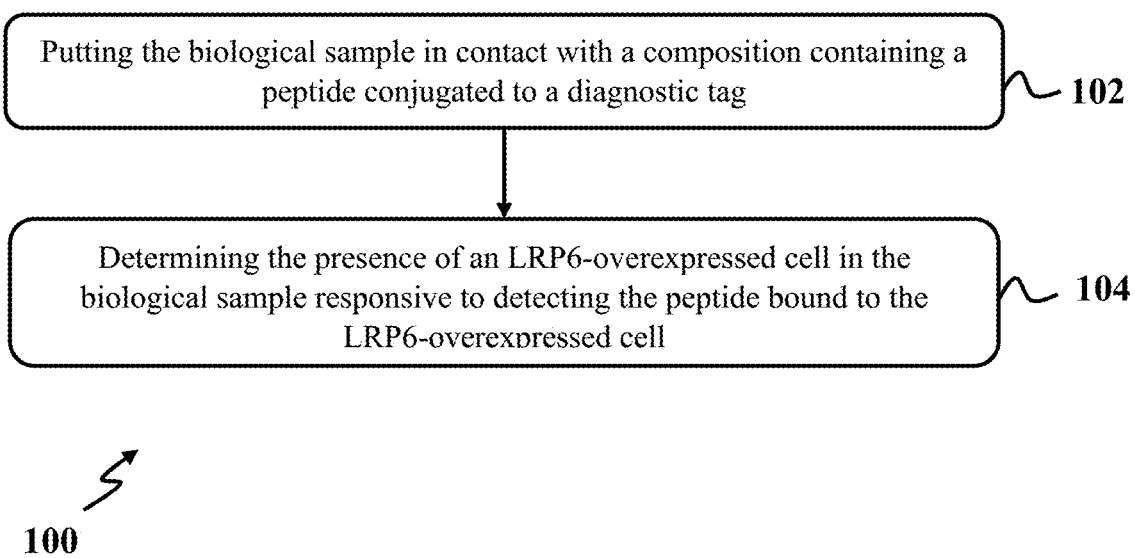
FIG. 1 illustrates a flowchart of an exemplary method for detecting LRP6-overexpressed cells in a biological sample, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Using small peptides for targeting receptors overexpressed in tumor cells has received much attention for treating cancers. Dickkopf-related protein 1 (DKK1) may bind to low-density lipoprotein receptor-related protein 6 (LRP6) and inhibit the Wnt signaling pathway in normal cells. Thus, administering DKK1-derived inhibitors to abnormal cells with overexpression of LRP6 may modulate the Wnt signaling pathway, inhibiting the cells' proliferation. However, conventional inhibitors of the Wnt signaling pathway may have limited efficiency due to their unfavorable properties, such as large size, low penetration into tumor tissues, and expensive and complicated production process. In the present disclosure, exemplary DKK1-derived peptides with small sizes may be capable of effectively targeting and killing LRP6-overexpressed cells in both in-vitro and in-vivo.

Disclosed herein is an exemplary composition for targeting LRP6-overexpressed cells. In an exemplary embodiment, exemplary composition may include an exemplary peptide. In an exemplary embodiment, the LRP6-overexpressed cells may include LRP6-overexpressed cells of at least one of colorectal cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, and bladder cancer. In the present disclosure, "overexpressed" refers to be produced in abnormally large amounts.

In an exemplary embodiment, exemplary peptide may include at least one of SEQ ID NO: 1 and SEQ ID NO: 3. In an exemplary embodiment, exemplary composition may further include at least one of SEQ ID NO: 2 and SEQ ID NO: 4. In an exemplary embodiment, exemplary peptides may antagonize the Wnt signaling pathway by interfering with binding a Wnt ligand to LRP6 receptors. In an exemplary embodiment, exemplary peptide may have a binding affinity to LRP6 with a dissociation constant (Kd) between about 1 µM and about 1000 µM. In an exemplary embodiment, binding exemplary peptide to the LRP6 receptor of the LRP6-overexpressed cells may block the Wnt signaling pathway and decrease the proliferation of the LRP6-overexpressed cells.

In an exemplary embodiment, exemplary composition may further include a tag conjugated to exemplary peptide. In an exemplary embodiment, the tag may include at least one of a therapeutic tag and a diagnostic tag. In an exemplary embodiment, the diagnostic tag may include at least one of a radioactive substance, a dye, a contrast agent, a fluorophore molecule, a nanoparticle, a bioluminescent molecule, an affinity agent, and a magnetic agent. In an exemplary embodiment, the radioactive substance may include at least one of phosphorus-32 (32P), sulfur-35 (35S), and phosphorus-33 (33P).

In an exemplary embodiment, the contrast agent may include at least one of gadolinium nanoparticles and superparamagnetic iron oxide nanoparticles. In an exemplary embodiment, the fluorophore molecule may include at least one of acridine orange, auramine, crystal violet, malachite green, porphin, phthalocyanine, cresyl violet, fluorescein, cyanine, phenylalanine, tyrosine, tryptophan, and rhodamine. In an exemplary embodiment, the bioluminescent molecule may include luciferase. In an exemplary embodiment, the affinity tag may include at least one of a streptavidin/biotin-based tag, a polyhistidine tag, and a maltose-binding protein (MBP) tag. In an exemplary embodiment, the nanoparticle may include at least one of superparamagnetic nanoparticles, gold nanoparticles, carbon nanotubes, silica nanoparticles, metal nanoparticles, graphene oxide nanoparticles, and metal-organic frameworks.

In an exemplary embodiment, an exemplary composition may be used for targeted drug delivery to LRP6-overexpressed cells. In an exemplary embodiment, the therapeutic tag may include at least one of a chemotherapeutic drug, a toxin, an anticancer growth inhibitor compound, an anticancer siRNA, and an anticancer antagomir. In an exemplary embodiment, the chemotherapeutic drug may include at least one of cisplatin, paclitaxel, carboplatin, topotecan, 5-fluorouracil, mitomycin C, docetaxel, oxaliplatin, epirubicin, cyclophosphamide, methotrexate, doxorubicin, and irinotecan. In an exemplary embodiment, an exemplary composition may further include a pharmaceutical carrier. In an exemplary embodiment, the carrier may include at least one of poly (lactic-co-glycolic acid) (PLGA) nanoparticles, hydrogels, micelles, dendrimers, polymeric carriers, magnetic carriers, carbon carriers, viral carriers, gold carriers, liquid crystals, nanocapsules, nanospheres, nisomes, ethosomes, liquid nanoparticles, nanoemulsions, microemulsions, carbon nanotubes, pronisosomes, proliposomes, transferosomes, protransferosomes, metal nanoparticles, mesoporous silica nanoparticles, chelators, and liposomal nanoparticles.

An exemplary composition may be used for in-vivo targeting the LRP6-overexpressed cells in diagnostic, therapeutic, and theragnostic applications. In an exemplary embodiment, the present disclosure describes an exemplary method for targeting LRP6-overexpressed cells in a subject. In an exemplary embodiment, exemplary method may include administering an effective amount of an exemplary composition to the subject. In an exemplary embodiment, an exemplary composition may include an exemplary peptide and a tag conjugated to exemplary peptide. In an exemplary embodiment, the tag may include at least one of a diagnostic tag and a therapeutic tag. In an exemplary embodiment, exemplary peptide may include at least one of SEQ ID NO: 1 and SEQ ID NO: 3. In an exemplary embodiment, exemplary peptide may further include at least one of SEQ ID NO: 2 and SEQ ID NO: 4.

In an exemplary embodiment, the subject may include at least one of a human and an animal. In an exemplary embodiment, the animal may include human, mouse, rat, dog, cat, bovine, and equine. In an exemplary embodiment, administering the effective amount of exemplary composition to the subject may include at least one of intravenous, intratumoral, intradermal, intramuscular, subcutaneous, rectal, and oral administration. In an exemplary embodiment, exemplary method may further include killing the LRP6-overexpressed cells in the subject by conducting at least one of magnetic hyperthermia, photodynamic therapy, and photothermal therapy. In an exemplary embodiment, an exemplary method for targeting the LRP6-overexpressed cells in a subject may further include tracking the LRP6-overexpressed cells in the subject using a biosensor and magnetic resonance imaging (MRI).

An exemplary composition may be used for in-vitro detection of the LRP6-overexpressed cells in a biological sample. FIG. 1 illustrates a flowchart of an exemplary method 100 for detecting LRP6-overexpressed cells in a biological sample, consistent with one or more exemplary embodiments of the present disclosure. An exemplary method 100 may include putting the biological sample in contact with exemplary composition containing the diagnostic tag conjugated to exemplary peptide (step 102) and determining the presence of an LRP6-overexpressed cell in the biological sample responsive to detecting exemplary peptide bound to the LRP6-overexpressed cell (step 104).

In further detail with respect to step 102, in an exemplary embodiment, putting the biological sample in contact with an exemplary composition may include forming antagonist-receptor complexes of exemplary peptide and the LRP6 receptors on the surfaces of the LRP6-overexpressed cells. In an exemplary embodiment, forming antagonist-receptor complexes of exemplary peptide and the LRP6 receptors may include forming antagonist-receptor complexes between exemplary peptide and the LRP6 receptors if the LRP6-overexpressed cell is present in the biological sample. In an exemplary embodiment, putting the biological sample in contact with exemplary composition may include putting at least one of a blood sample, a plasma sample, a serum sample, a urine sample, a fecal sample, a cervix sample, and a semen sample in contact with exemplary composition.

In further detail with respect to step 104, in an exemplary embodiment, detecting exemplary peptide bound to the LRP6-overexpressed cell may include detecting a signal generated by the diagnostic tag responsive to binding exemplary peptide to the LRP6-overexpressed cell. In an exemplary embodiment, the signal may include at least one of a biological signal, a chemical signal, a fluorescent signal, an electrochemical signal, and a physical signal.

In an exemplary embodiment, detecting exemplary peptide bound to LRP6-overexpressed cell may include detecting exemplary peptide bound to the LRP6-overexpressed cell by conducting at least one of a chemiluminescent assay, an immunofluorescent assay, enzyme-linked immunosorbent assay (ELISA), radioimmunoassay, a Western blot assay, an immunoblots assay, a gel electrophoresis assay, an enzyme immunoassay, an immunoprecipitation assay, an immunohistochemical assay, an immunochromatographic assay, a dot blot assay, a slot blot assay, confocal imaging, laser scanning microscopy, fluorescent microscopy, fluorescent affinity chromatography, fluorescent size exclusion chromatography, fluorescent based filtration, fluorescent-based centrifugation, fluorescence correlation spectroscopy (FCS), fluorescence polarization assay, ligand-receptor fluorescence resonance energy transfer assay, and flow cytometry.

EXAMPLES

Example 1: Design of Inhibitory Peptides for Targeting LRP6-Overexpressed Cells

The Wnt signaling pathway may be considered as the most significant signaling pathway activated in various cancers. This pathway may be blocked by various proteins, such as DKK proteins, which disrupt the LRP6-Frizzled complex as the initiation complex. Therefore, a computational study was implemented to design inhibitory peptides against LRP6 receptors.

At first, hotspot amino acids of the human LRP6-DKK1 complex were determined by alanine scanning. Alanine computational scanning is a free energy function-based method used to analyze amino acids in hot regions in protein-ligand interactions. The crystallography structure of human LRP6-DKK1 (PDB ID: 3S2K) was obtained from protein data bank (PDB) with a resolution of 2.9 Angstrom, and amino acids involved in the interaction between the LRP6 and the DKK1 were extracted using Ligplot+ software, a program to graph protein-ligand interaction (LIGPLOT) and protein-protein interaction (DIMPLOT).

Alanine scanning of the human LRP6-DKK1 complex was performed to find the amino acids of DKK1 in the interaction with the LRP6 receptor using the Robetta alanine scanning program. On the Robetta server, positive values predict the destabilizing effect on the complex resulting from the substitution of amino acids with alanine, and negative values indicate the stabilizing effect on the complex. Predicted amino acids whose free energy of binding due to alanine mutations increased by more than 1 kcal/mol are considered hot spots. The alanine scanning revealed amino acids Arg191, Lys222, Arg224, Arg225, Lys226, His229, and Ser244 from DKK1 and amino acids Glu663, Ser665, Tyr706, Asp748, Lys770, Leu810, His834, Trp850, and Tyr875 amino acids from LRP6 as hot spot regions.

In the next step, the peptide library of the DKK1 carboxy-terminal was designed for LRP6 inhibition using BackRub and sequence tolerance protocols in the Rosetta 3.5 software. In the Rosetta 3.5 software, two sets of sequence positions were used for creating residue files (resfiles). The first set of sequence positions included amino acids that remained the same for all subsequent simulations as the interaction positions. The second set of sequence positions included the positions that may have various amino acid types by any of the 20 canonical amino acids. By adjusting the resfiles, the interacting amino acids' position, including amino acids 203, 208, and 211, were preserved for the first fragment, and other amino acids were substituted with any standard amino acids. In a second fragment, the amino acids at positions 222, 223, 224, 226, 236, and 238 were preserved, and other amino acid positions were allowed to be substituted with any of the standard amino acids.

In the next step, a combination of simulated annealing and genetic algorithm optimization methods was used to enrich the ensemble's members' low-energy sequences. The generated sequences were sorted based on the energy score in the R package. Three-dimensional structures of the high score peptides with the lowest energy were predicted by using the PEP-Fold program. Also, a fragment of the carboxyl-terminal of DKK1 containing two cysteine amino acids in its ends was cyclized using the YASARA program and selected as pep-4 (SEQ ID NO: 4). Also, a fragment with a natural sequence of DKK1 in the beta-sheet structure was chosen as pep-2 (SEQ ID NO: 2).

Figure 2A:
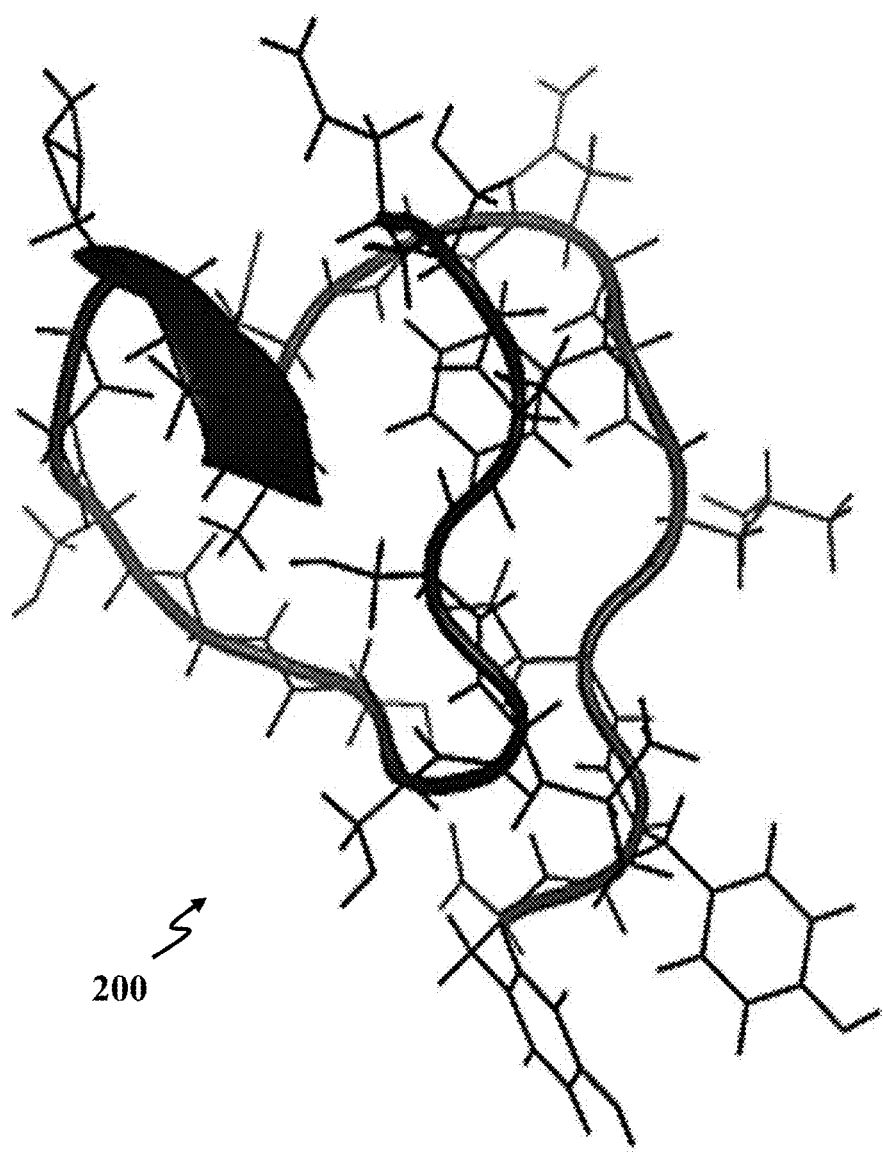
FIG. 2A illustrates a schematic view of a tertiary structure 200 of an exemplary peptide (SEQ ID NO: 1) for targeting low-density lipoprotein receptor-related protein 6 (LRP6)-overexpressed cells, consistent with one or more exemplary embodiments of the present disclosure.
Figure 2B:
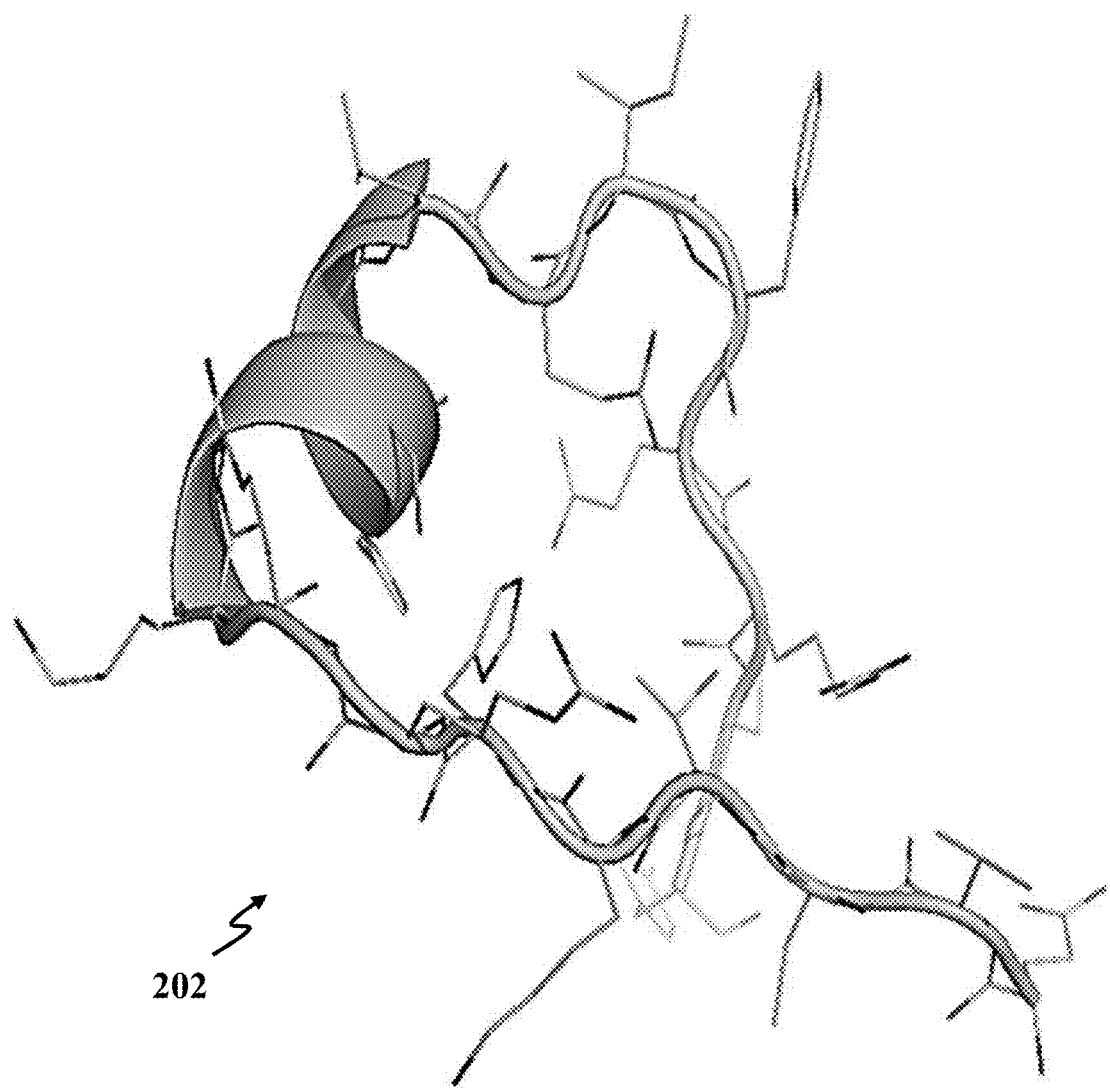
FIG. 2B illustrates a schematic view of a tertiary structure 202 of an exemplary peptide (SEQ ID NO: 2) for targeting LRP6-overexpressed cells, consistent with one or more exemplary embodiments of the present disclosure.

FIG. 2A illustrates a schematic view of a tertiary structure 200 of an exemplary peptide (SEQ ID NO: 1) for targeting low-density lipoprotein receptor-related protein 6 (LRP6)-overexpressed cells, consistent with one or more exemplary embodiments of the present disclosure. Referring to FIG. 2A, exemplary peptide (SEQ ID NO: 1) may have a coil-alpha helix structure 200 with the free energy of binding (binding affinity) of about −8.4 (kcal/mol) and dissociation constant ($K_D$) of about $1.1 \times 10^{-7}$ (M). FIG. 2B illustrates a schematic view of a tertiary structure 202 of an exemplary peptide (SEQ ID NO: 2) for targeting LRP6-overexpressed cells, consistent with one or more exemplary embodiments of the present disclosure. Referring to FIG. 2B, exemplary peptide (SEQ ID NO: 2) may have a coil-alpha helix structure 202 with the binding affinity of about −8.2 (kcal/mol) and $K_D$ of about $3.9 \times 10^{-7}$ (M).

Figure 2C:
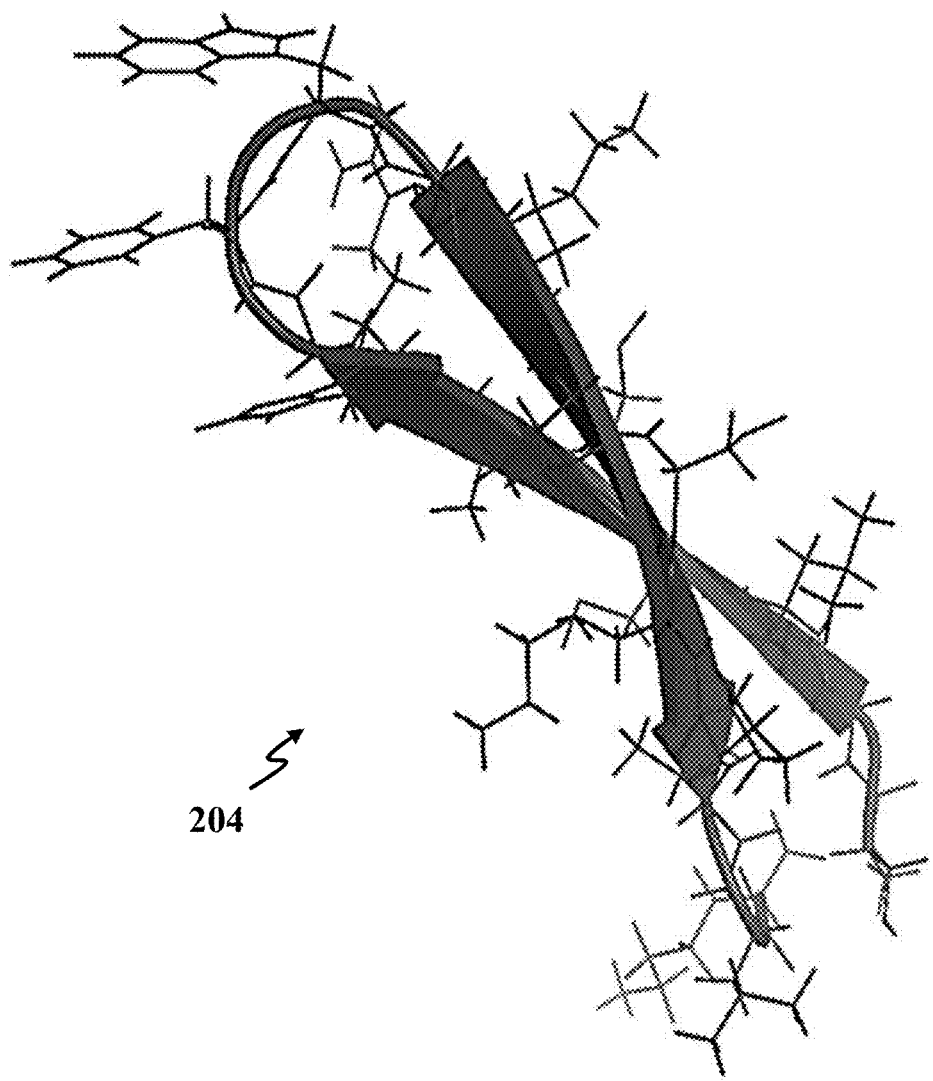
FIG. 2C illustrates a schematic view of a tertiary structure 204 of an exemplary peptide (SEQ ID NO: 3) for targeting LRP6-overexpressed cells, consistent with one or more exemplary embodiments of the present disclosure.
Figure 2D:
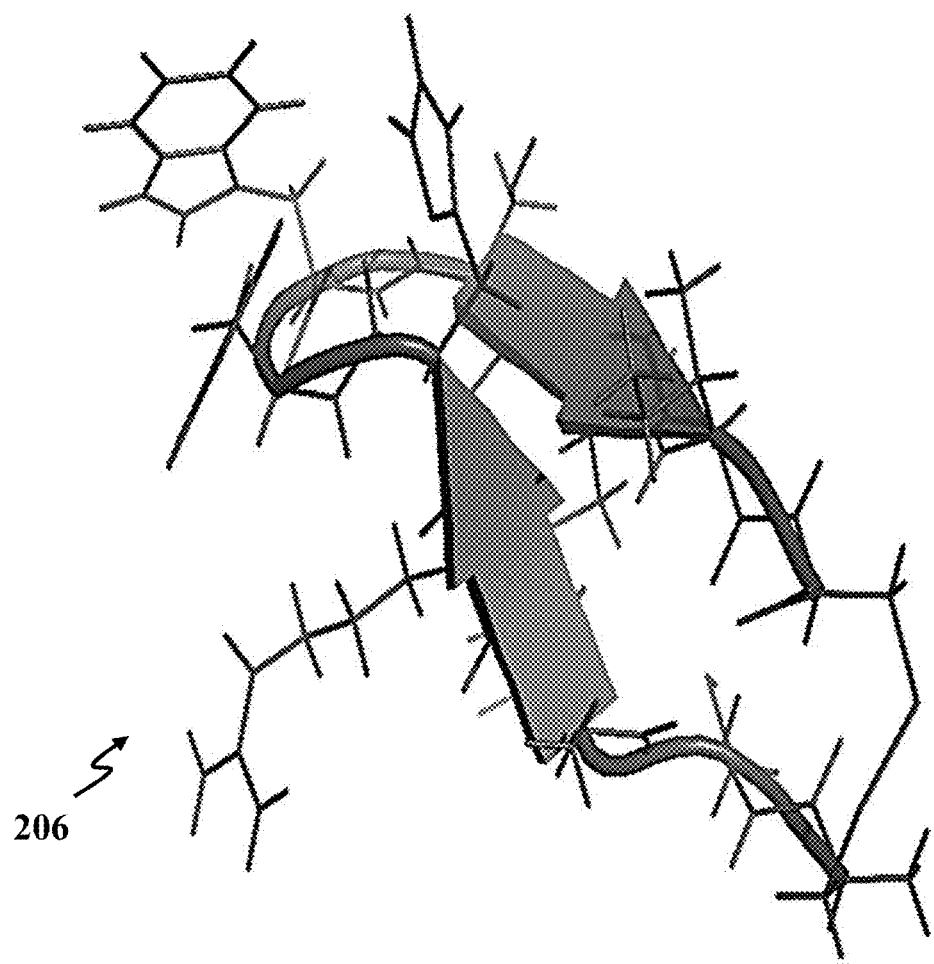
FIG. 2D illustrates a schematic view of a tertiary structure 206 of an exemplary peptide (SEQ ID NO: 4) for targeting LRP6-overexpressed cells, consistent with one or more exemplary embodiments of the present disclosure.

FIG. 2C illustrates a schematic view of a tertiary structure 204 of an exemplary peptide (SEQ ID NO: 3) for targeting LRP6-overexpressed cells, consistent with one or more exemplary embodiments of the present disclosure. Referring to FIG. 2C, exemplary peptide (SEQ ID NO: 3) may have a structure 204 including two anti-parallel beta-sheets with binding affinity of about −7.8 (kcal/mol) and $K_D$ of about $5.5 \times 10^{-7}$ (M). FIG. 2D illustrates a schematic view of a tertiary structure 206 of an exemplary peptide (SEQ ID NO: 4) for targeting LRP6-overexpressed cells, consistent with one or more exemplary embodiments of the present disclosure. Referring to FIG. 2D, exemplary peptide (SEQ ID NO: 4) may have a structure 206 including two antiparallel beta-sheets with the binding affinity of about −8.5 (kcal/mol) and $K_D$ of about $5.4 \times 10^{-7}$ (M).

Example 2: Molecular Dynamic Simulation of Complexes Exemplary Peptides with LRP6

In this example, molecular dynamics (MD) simulation was performed using GROMACS 5.0.6 package to minimize the energy of the components and optimizing the structure of the peptides individually and in complex with the A chain of the LRP6. Parameter files were created using the AMBER99SB-ILDN force field, and the TIP3P model was used as the water model throughout the simulation. The MD simulation was run on an AMD 8 GHz processor at 300 Kelvin. System preparation for simulation includes system energy minimization by taking advantage of steep descent with a tolerance of 10 kJ/mol/nm in 2 femtoseconds (fs) step size. In the position-restrained step, all hydrogen atoms were allowed to relax with fixed heavy atoms for 50 ps with a step size of 2 fs. All bonds were constrained using the linear constraint solver (LINCS) algorithm. A smooth particle mesh Ewald (PME) method was applied to calculate the electrostatic interactions with a grid spacing of 0.16 nm and Van der Waals (VDW) interactions with 1.4 nm cutoff as the certain cutoff distance which is used in solvent-accessible surface areas (SASA) calculation. Simulations were performed with a 2 fs time step for 20 ns.

A comparative analysis of each trajectory's time-dependent properties was performed for mean square root deviation (RMSD), solvent-accessible surface areas (SASA), and variations of the girder radius. Root mean square fluctuation (RMSF) were calculated by averaging for each amino acid. Hydrogen bonds were measured during the last 10 nanoseconds of each MD trajectory using cutoffs of 3.5° A for donor-acceptor distance. The electrostatic and Van der Waals energy around peptides were calculated for the snapshot structures of the peptides extracted from the protein-peptide simulations during the last 5 ns MD (at 10 ps intervals) using the HADDOCK web server.

TABLE 1

Stability, flexibility, and surface exposed to the solvent of exemplary peptide structures obtained using MD simulation

| | Protein Backbone RMSD (nm) | | RMSF to Wild Type (nm) | | Solvent accessible surface area (nm$^2$) | |
|---|---|---|---|---|---|---|
| | peptide | complex | peptide | complex | peptide | Complex |
| Pep-1 | 0.3 | 0.28 | 0.4 | 0.46 | 29.5 | 141.21 |
| Pep-2 | 0.23 | 0.21 | 0.24 | 0.22 | 27.16 | 135.78 |
| Pep-3 | 0.28 | 0.21 | 0.3 | 0.31 | 28.21 | 139.42 |
| Pep-4 | 0.2 | 0.28 | 0.17 | 0.15 | 26.36 | 131.27 |

Figure 3A:
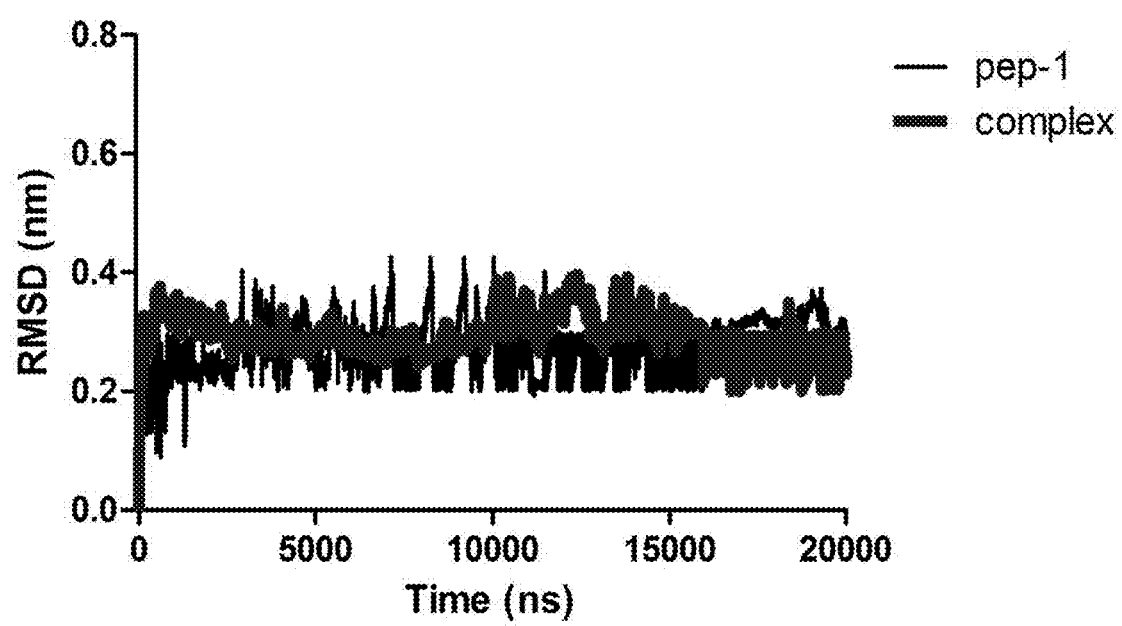
FIG. 3A illustrates mean square root deviation (RMSD) plots of pep-1 (SEQ ID NO: 1) in the presence or absence of the receptor after 20 ns of MD simulation, consistent with one or more exemplary embodiments of the present disclosure.
Figure 3B:
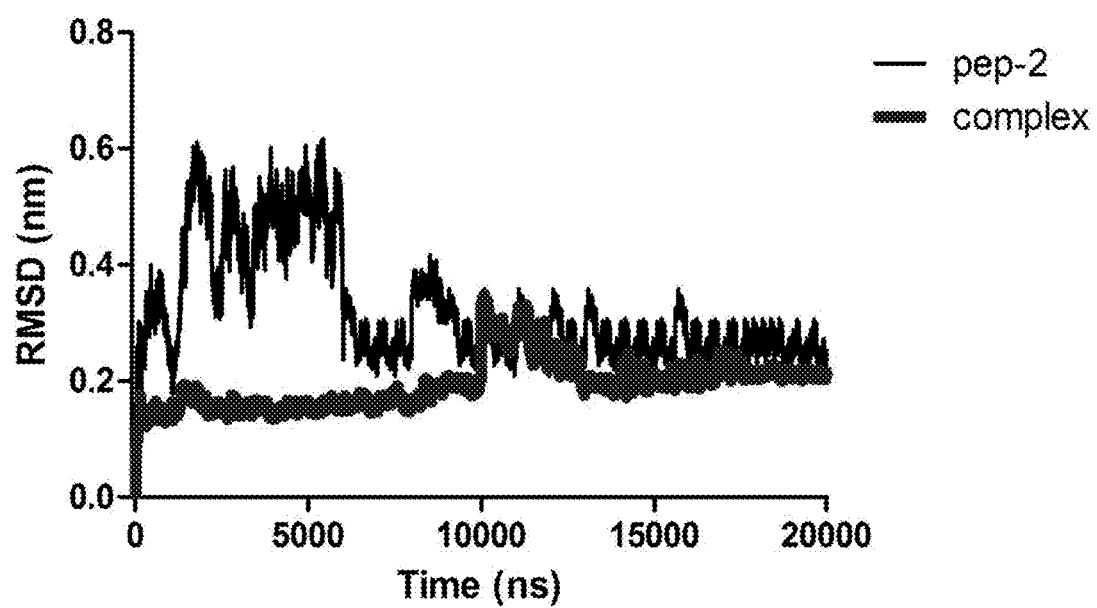
FIG. 3B illustrates RMSD plots of pep-2 (SEQ ID NO: 2) in the presence or absence of the receptor after 20 ns of MD simulation, consistent with one or more exemplary embodiments of the present disclosure.
Figure 3C:
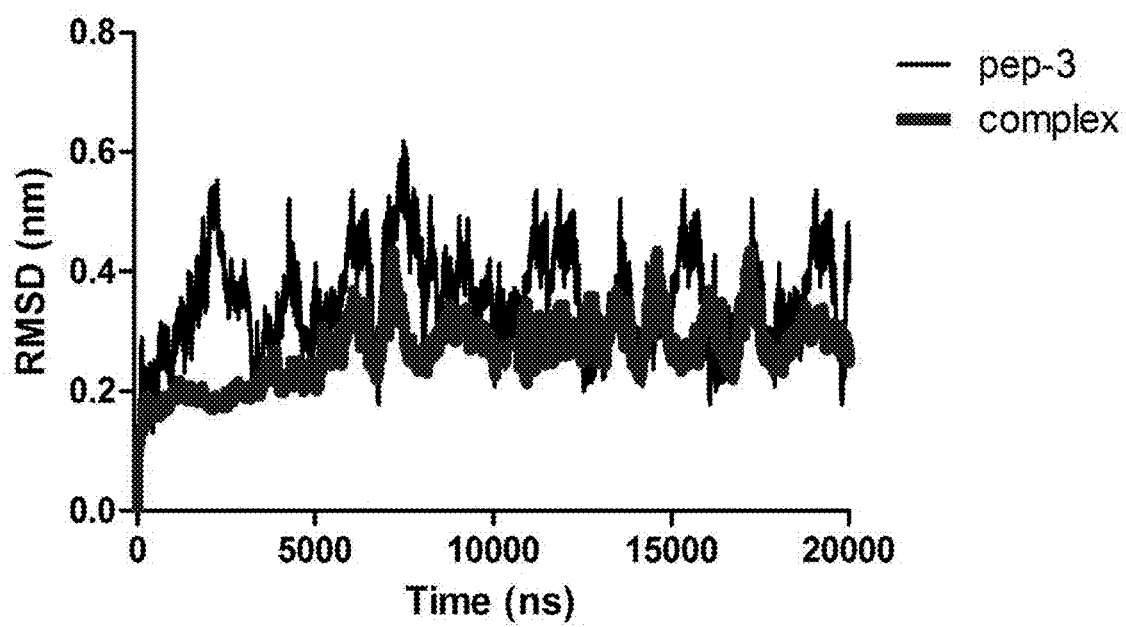
FIG. 3C illustrates RMSD plots of pep-3 (SEQ ID NO: 3) in the presence or absence of the receptor after 20 ns of MD simulation, consistent with one or more exemplary embodiments of the present disclosure.
Figure 3D:
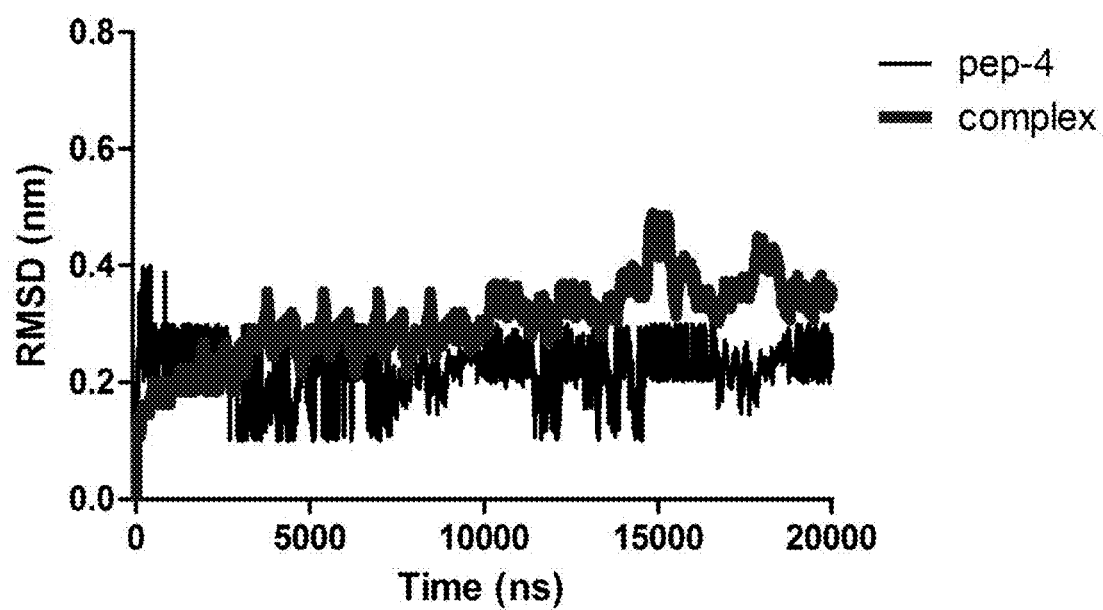
FIG. 3D illustrates RMSD plots of pep-4 (SEQ ID NO: 4) in the presence or absence of the receptor after 20 ns of MD simulation, consistent with one or more exemplary embodiments of the present disclosure.

RMSD is indicative of the stability of peptides and their convergence in structure in complex and non-complex mode. FIG. 3A illustrates RMSD plots of pep-1 (SEQ ID NO: 1) in the complexed state with LRP6 and the absence of the LRP6 after 20 ns of MD simulation, consistent with one or more exemplary embodiments of the present disclosure. FIG. 3B illustrates RMSD plots of pep-2 (SEQ ID NO: 2) in the complexed state with LRP6 and the absence of the LRP6 after 20 ns of MD simulation, consistent with one or more exemplary embodiments of the present disclosure. FIG. 3C illustrates RMSD plots of pep-3 (SEQ ID NO: 3) in the complexed state with LRP6 and the absence of the LRP6 after 20 ns of MD simulation, consistent with one or more exemplary embodiments of the present disclosure. FIG. 3D illustrates RMSD plots of pep-4 (SEQ ID NO: 4) in the complexed state with LRP6 and the absence of the LRP6 after 20 ns of MD simulation, consistent with one or more exemplary embodiments of the present disclosure.

Referring to FIGS. 3A-3D and TABLE 1, the values of RMSD in the presence and absence of the receptor were between 0.2-0.7 and 0.15-0.82, respectively. Lower values of RMSD indicated more stability in the simulated system. The RMSD values showed that the conformation of all fragments in both complexed states with the receptor and the receptor's absence reached equilibrium after 20 ns of molecular dynamics simulation. In other words, each exemplary peptide complex with LRP6 became stable and folded during the MD simulation.

Figure 4A:
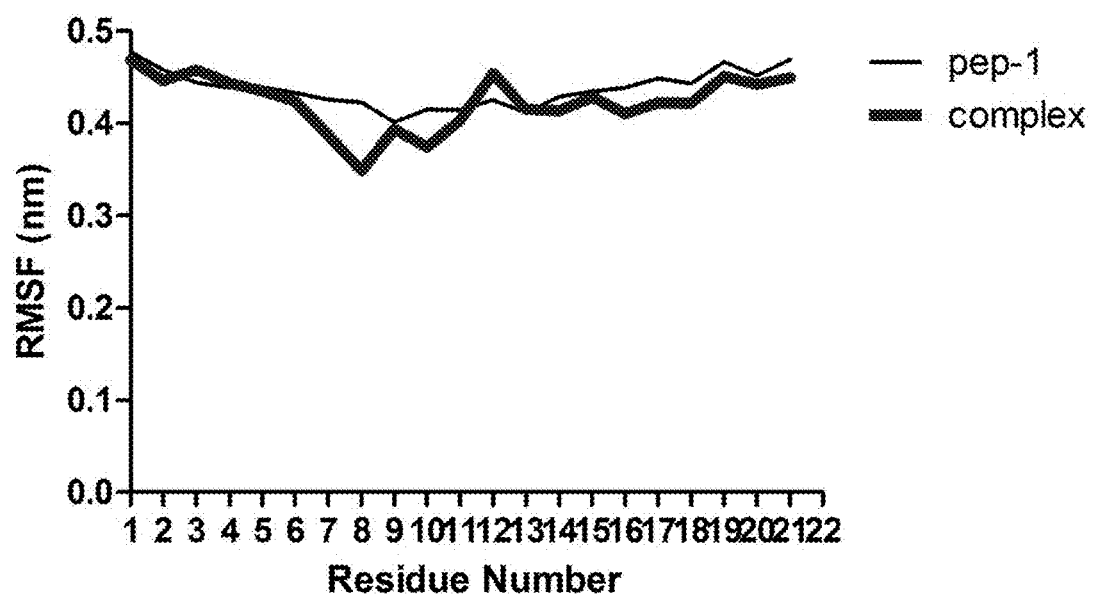
FIG. 4A illustrates root mean square fluctuation (RMSF) plots of pep-1 (SEQ ID NO: 1) in the complexed state with LRP6 and the absence of the LRP6, consistent with one or more exemplary embodiments of the present disclosure.
Figure 4B:
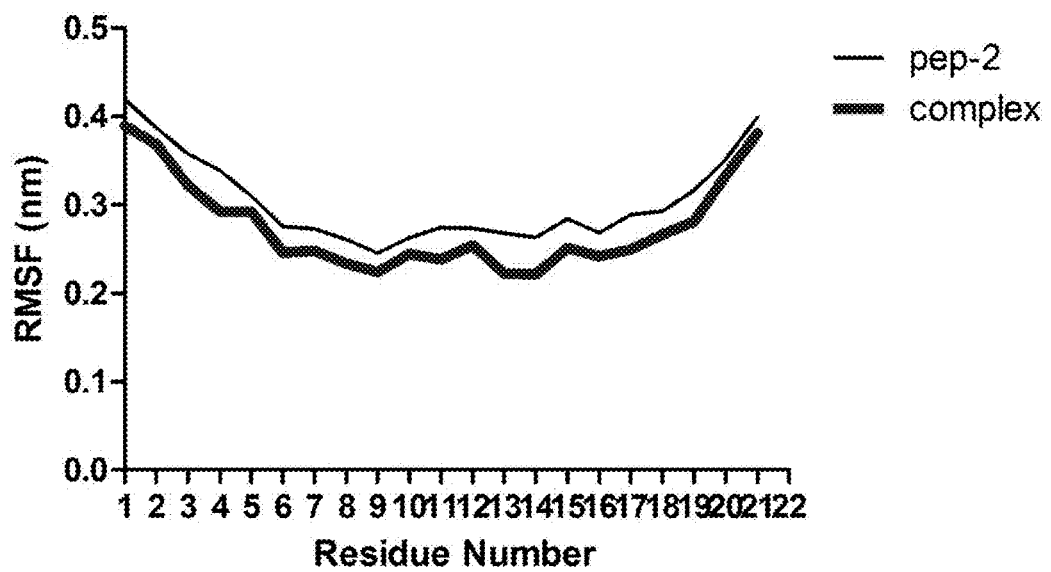
FIG. 4B illustrates RMSF plots of pep-2 (SEQ ID NO: 2) in the complexed state with LRP6 and the absence of the LRP6, consistent with one or more exemplary embodiments of the present disclosure.
Figure 4C:
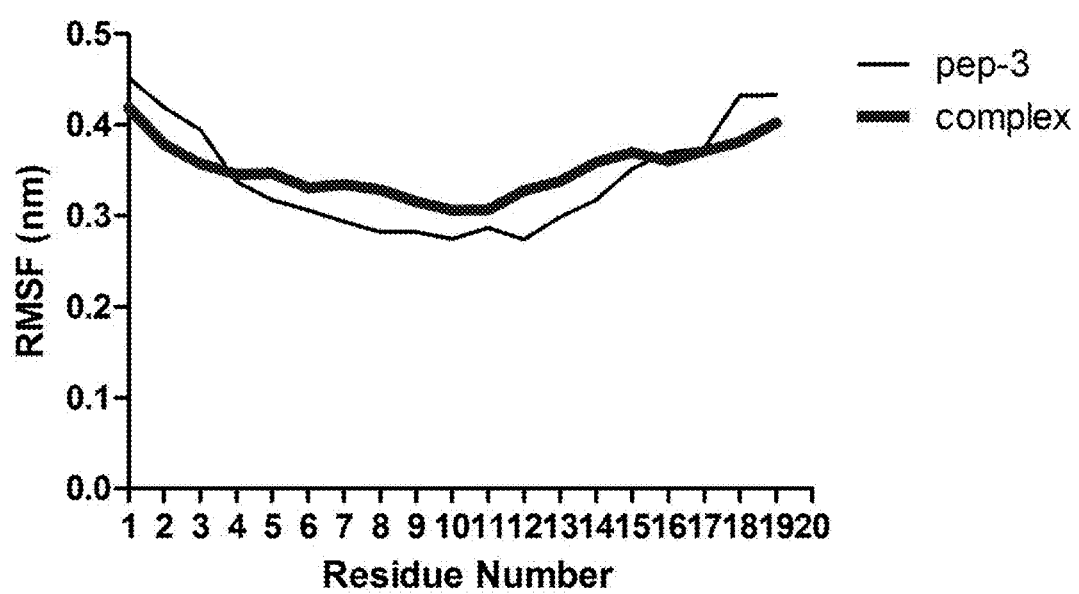
FIG. 4C illustrates RMSF plots of pep-3 (SEQ ID NO: 3) in the complexed state with LRP6 and the absence of the LRP6, consistent with one or more exemplary embodiments of the present disclosure.
Figure 4D:
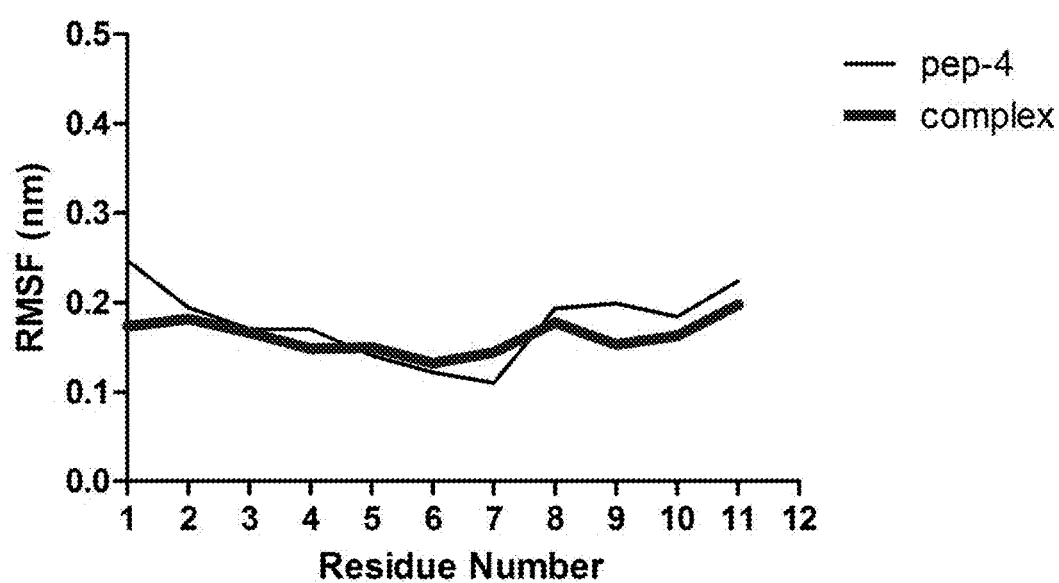
FIG. 4D illustrates RMSF plots of pep-4 (SEQ ID NO: 4) in the complexed state with LRP6 and the absence of the LRP6, consistent with one or more exemplary embodiments of the present disclosure.

RMSF values were used to evaluate the flexibility of structures in a complex and non-complex mode. FIG. 4A illustrates RMSF plots of pep-1 (SEQ ID NO: 1) in the complexed state with LRP6 and the absence of the LRP6, consistent with one or more exemplary embodiments of the present disclosure. FIG. 4B illustrates RMSF plots of pep-2 (SEQ ID NO: 2) in the complexed state with LRP6 and the absence of the LRP6, consistent with one or more exemplary embodiments of the present disclosure. FIG. 4C illustrates RMSF plots of pep-3 (SEQ ID NO: 3) in the complexed state with LRP6 and the absence of the LRP6, consistent with one or more exemplary embodiments of the present disclosure. FIG. 4D illustrates RMSF plots of pep-4 (SEQ ID NO: 4) in the complexed state with LRP6 and the absence of the LRP6, consistent with one or more exemplary embodiments of the present disclosure. Referring to FIGS. 4A-4D and TABLE 1, the flexibility of exemplary peptides in the complexed state with LRP6 and the absence of the LRP6 were verified. Estimating the level of exposure of the surface to the solvent as one of the important structural properties of proteins was measured via SASA. The RMSD and SASA values of the peptides individually and in complex with the receptor indicated a relationship between the changes of exemplary peptide structure and the complex's surface size. It means that the larger size of the interfaces leads to more conformational changes than the smaller interfaces.

The compactness and overall quality of the exemplary peptides were determined by calculating the radius of gyration (RoG). The RoG is used as a suitable criterion for the folding and unfolding of proteins. The analysis of polar and nonpolar area per energy of a peptide signified the relationship between the hydrophobicity and solvent accessibility, which illustrated that more nonpolar area was related to less solvent accessibility. In contrast, polar areas tended to occur where solvent accessibility was high.

TABLE 2

Compactness and polarity of exemplary peptides after MD simulation

| | Radius of Gyration (nm) | | Polar area/energy (nm$^2$) | | Apolar area/energy (nm$^2$) | |
|---|---|---|---|---|---|---|
| | Peptide | Complex | Peptide | Complex | Peptide | Complex |
| Pep-1 | 0.6 | 1.46 | 982.56 | 12487.29 | 1172.79 | 15387 |
| Pep-2 | 0.74 | 1.8 | 1086.97 | 11945.5 | 1698.61 | 15122.35 |
| Pep-3 | 0.63 | 1.32 | 862.52 | 12087.58 | 1774.53 | 15764.42 |
| Pep-4 | 0.71 | 1.43 | 600.25 | 9524.30 | 886.10 | 15311.42 |

Figure 5A:
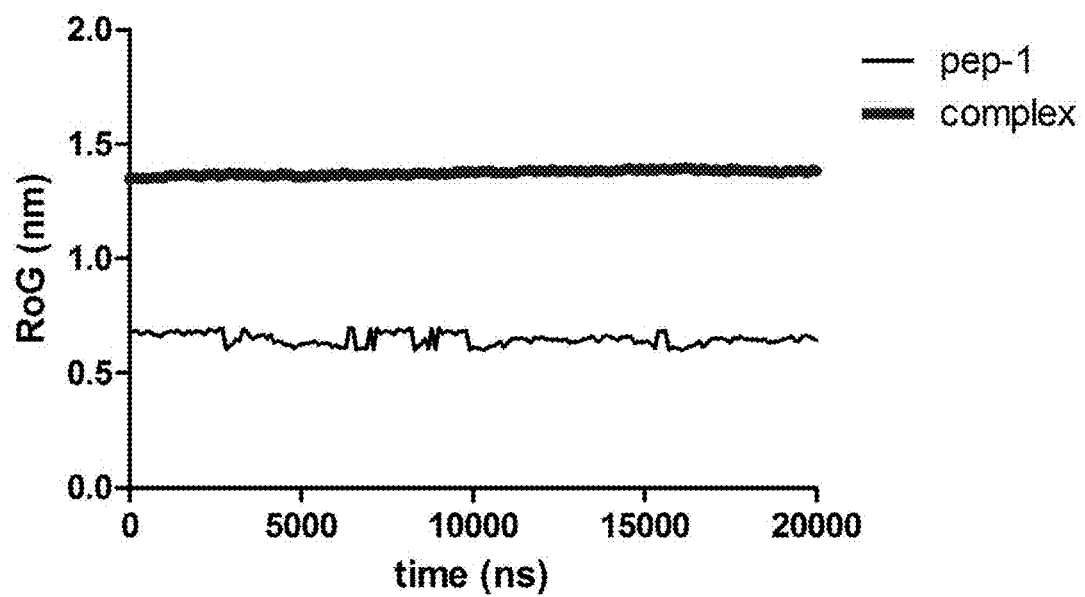
FIG. 5A illustrates radius of gyration (RoG) plots of pep-1 (SEQ ID NO: 1) in the complexed state with LRP6 and the absence of the LRP6, consistent with one or more exemplary embodiments of the present disclosure.
Figure 5B:
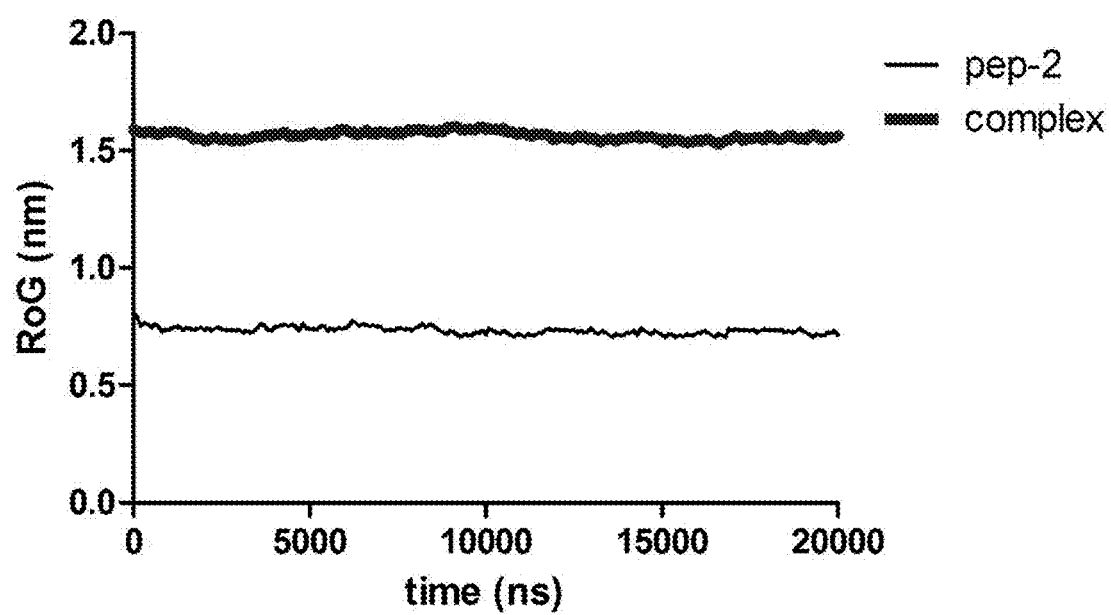
FIG. 5B illustrates RoG plots of pep-2 (SEQ ID NO: 2) in the complexed state with LRP6 and the absence of the LRP6, consistent with one or more exemplary embodiments of the present disclosure.
Figure 5C:
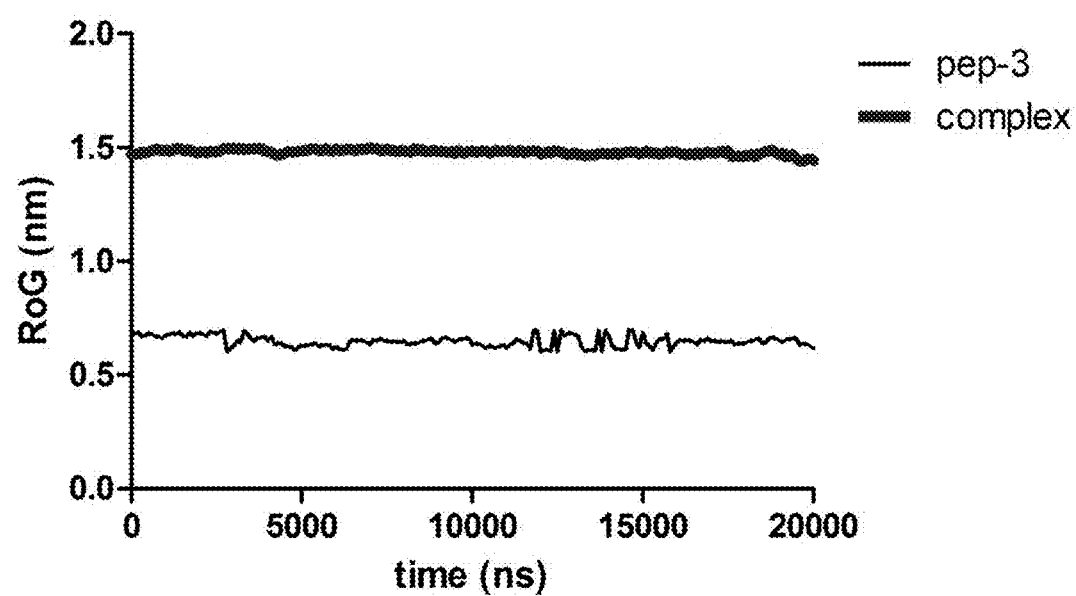
FIG. 5C illustrates RoG plots of pep-3 (SEQ ID NO: 3) in the complexed state with LRP6 and the absence of the LRP6, consistent with one or more exemplary embodiments of the present disclosure.
Figure 5D:
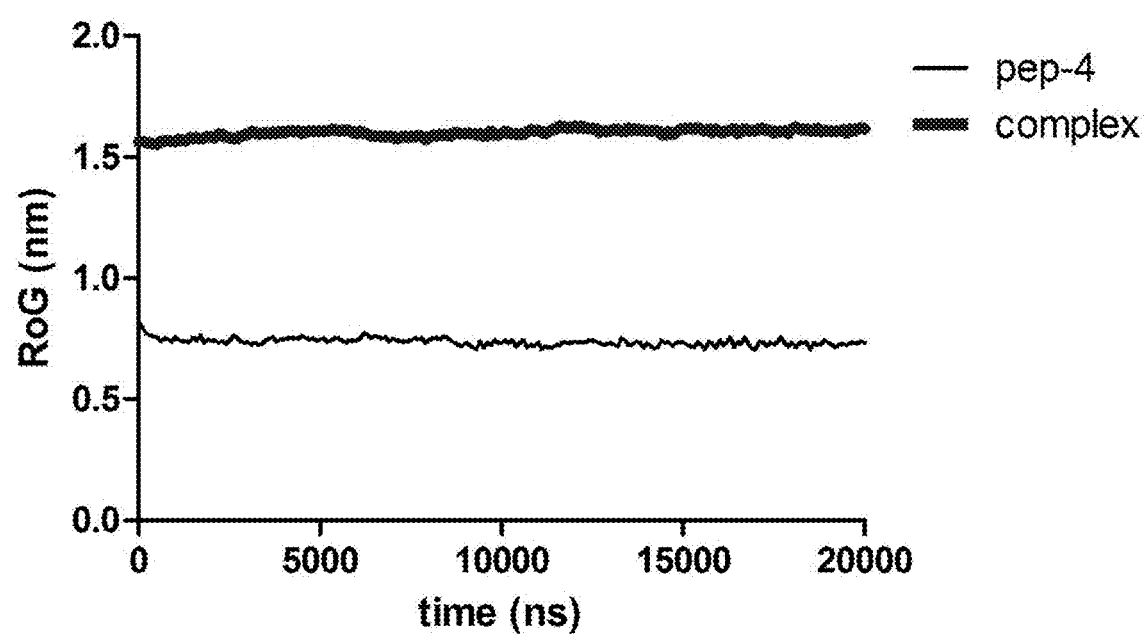
FIG. 5D illustrates RoG plots of pep-4 (SEQ ID NO: 4) in the complexed state with LRP6 and the absence of the LRP6, consistent with one or more exemplary embodiments of the present disclosure.

FIG. 5A illustrates RoG plots of pep-1 (SEQ ID NO: 1) in the complexed state with LRP6 and the absence of the LRP6, consistent with one or more exemplary embodiments of the present disclosure. FIG. 5B illustrates RoG plots of pep-2 (SEQ ID NO: 2) in the complexed state with LRP6 and the absence of the LRP6, consistent with one or more exemplary embodiments of the present disclosure. FIG. 5C illustrates RoG plots of pep-3 (SEQ ID NO: 3) in the complexed state with LRP6 and the absence of the LRP6, consistent with one or more exemplary embodiments of the present disclosure. FIG. 5D illustrates RoG plots of pep-4 (SEQ ID NO: 4) in the complexed state with LRP6 and the absence of the LRP6, consistent with one or more exemplary embodiments of the present disclosure.

Referring to FIGS. 5A-5D and TABLE 1, the results show that the structures' overall shape and size remained stable throughout the study. Exemplary peptides appeared to be more accessible for binding to the receptor in the complex with the receptor than in the single state. In other words, the peptide is more likely to be compressed in the absence of the receptor. On the other hand, RoG and SASA values displayed a relationship between the fluctuation of protein and the surface accessible to solvent, while a larger RoG leads to the more accessible surface area.

Example 3: In-Silico Analysis of Exemplary Peptides

In this example, different features of exemplary peptides, such as binding affinity to LRP6, half-life, and stability, cell permeability, physicochemical characteristics, and toxicity, were predicted using in-silico bioinformatic analysis. Analysis and visualization of docking results were done using PyMol software. Physicochemical characteristics of exemplary peptides were also calculated using the EXPASY webserver (ProtParam). The physicochemical characteristics included molecular weight, theoretical PI, estimated half-life, instability index, aliphatic index, mean hydrophobicity, and cell permeability. The binding affinity of exemplary peptides to LRP6 was determined by performing molecular docking using ClusPro and HADDOCK web server. ClusPro output is a shortlist of cluster-based peptide-receptor complexes. It presents models of different receptor-peptide positions relative to each other by calculating the central binding energy.

Also, binding affinity and dissociation constant ($K_D$) were predicted based on the protein-peptide complex's structural properties via the PRODIGY web server. The predicted ΔG in PRODIGY was calculated based on the number and type of interfacial contacts (ICs) found at the interface between receptor and peptide and the amount of the non-interacting surface (NIS) in a protein-protein complex. The ICs may be classified as polar, nonpolar, and charged interacting residues. Then, each peptide's KD was determined based on the free energy of binding between the peptide and the receptor (ΔG). TABLE 3 represents the number of hydrogen (H-bond) and non-hydrogen (nonpolar) bonds involved in the peptide-receptor interaction.

TABLE 3

Results of docking by Cluspro, Haddock, and Prodigy after Backrub

| Peptide Name | [1]ClusPro-lowest energy | H-bonds AA | Nonpolar | ΔG (kcal/mol) | $K_D$ (M) |
|---|---|---|---|---|---|
| Pep-1 (SEQ ID NO: | −1305.7 | 9 | 9 | −8.4 | $1.1 \times 10^{-7}$ |
| Pep-2 (SEQ ID NO: | −1288.6 | 7 | 5 | −8.2 | $3.9 \times 10^{-7}$ |
| Pep-3 (SEQ ID NO: | −1198.7 | 5 | 3 | −7.8 | $5.5 \times 10^{-7}$ |
| Pep-4 (SEQ ID NO: | −785.1 | 5 | 12 | −8.5 | $5.4 \times 10^{-7}$ |

[1]Central energy binding of peptides to receptors while the putative structure is clustered together Referring to TABLE 3, the lowest energy docked structure is close to the native structure of the complex of peptide-LRP6. Also, number of hydrogen bonds and hydrophobic (non-polar) interactions, the predicted ΔG (binding affinity) values, and the $K_D$ of peptides were acceptable. The smaller the $K_D$ value, the greater the binding affinity of the peptide for its target.

Ramachandran (phi against psi) plot shows the stereo-chemical quality of amino acid-based on torsion angel. Peptide structures were validated by studying the backbone's torsion angles (phi and psi) via PROCHECK software and Verify3D (TABLE 4). Finally, peptides' stability and binding free energy were determined by calculating interaction energy using FoldX software. Higher values in interaction energy and Verify3D were indicative of more stable compounds. The amino acids in binding sites of the LRP6 and exemplary peptides are represented in TABLE 5.

TABLE 4

Van der Waals and electrostatic energy and output of Verify3D and interaction energy

| Peptide Name | Van der Waals energy | Electrostatic energy (kcal/mol) | PROCHECK (phi-psi) | Verify3D | Interaction Energy (kcal/Mol)[1] |
|---|---|---|---|---|---|
| Pep-1 | −62.80 | −492.10 | −2.24 | −5.14 | −10.2108 |
| Pep-2 | −60.00 | −524.30 | −1.42 | −9.63 | −10.1388 |
| Pep-3 | −66.50 | −512.60 | −1.61 | −7.87 | −7.57536 |
| Pep-4 | −20.2 | −169.3 | −1.59 | −11.88 | −1.92252 |

Referring to TABLE 4, Van der Waals energy includes attraction and repulsions between atoms, molecules, and surfaces, as well as other intermolecular forces. In electrostatic energy the electrostatic interactions that play a dominant role in the formation of protein-peptide interfaces is represented. Also, PROCHECK checks the stereo-chemical quality of a protein structure by analyzing its overall and residue-by-residue geometry. Verify3D determines the compatibility of an atomic model with its own amino acid sequence. In interaction energy, overall consistent relationship between the intermolecular interactions that hold the complex of the peptide and LRP6 together and the conformational properties of peptides is represented.

TABLE 5

Amino acids in binding sites of the LRP6 and exemplary peptides

| Pep-1 | Hydrophobic bonds | AA-DKK | Cys220, Lys215, Gln235 |
|---|---|---|---|
| | | LRP6E3 | Asp811, Thr812, Trp767, Trp850 |
| | H-bonds | AA-DKK | Val219, Arg224, Lys222, Tyr238, Arg236 |
| | | LRP6E3 | Arg792, Asn813, Asp811, His834, leu810 |
| | Hot spot | AA-DKK | Lys222, Arg224, Arg225, Lys226, His229, |
| | | LRP6E3 | Glu663, Ser665, Asp748, His834, Tyr875 |
| Pep-2 | Hydrophobic bonds | AA-DKK | Cys220, Arg236, Leu231, He233 |
| | | LRP6E3 | Asp811, Trp767, Asp811, Met877, Trp850 |
| | H-bonds | AA-DKK | Val219, Arg236, Arg224, Gly227, Ser228, |
| | | LRP6E3 | Glu663, Tyr706, Arg792, Leu810, Asn813, |
| | Hot spot regions | AA-DKK | Val219, Lys222, Arg224, Lys226, His229, |
| | | LRP6E3 | Glu663, Ser665, Asp748, Lys770, His834, |
| Pep-3 | Hydrophobic bonds | AA-DKK[1] LRP6 E3[2] | He209, Leu214, Lys215 Tyr706, Asn813, Thr812 |
| | H-bonds | AA-DKK | His204, Trp206, Lys211, Lys215, Arg203 |
| | | LRP6E3 | Glu708, Glu663, His834, Asp811, Tyr875 |
| | Hot spot regions | AA-DKK | Arg203, His204, Trp206, Lys208 |
| | | LRP6E3 | Glu663, Asp811, Asn813 |
| Pep-4 | Hydrophobic bonds | AA-DKK | Lys208, Ala202, Cys200, Phe205, Trp206 |
| | | LRP6E3 | He681, Tyr875, Met877, Leu810, Trp767, |

TABLE 5-continued

Amino acids in binding sites of the
LRP6 and exemplary peptides

| | | |
|---|---|---|
| H-bonds | AA-DKK | His204, Tyr206, Ser207, Lys208 |
| | LRP6E3 | Tyr706, Glu708, Glu663, Arg751, Ser682, |
| Hot spot regions | AA-DKK | Arg203, His204, Phe205, Trp206 |
| | LRP6E3 | Glu663, Ser665, Lys770, Trp850, Tyr875 |

[1]AA-DKK: amino acids of DKK,
[2]LRP6 E3: amino acids of E3 domain of LRP6

Predicting the toxicity of therapeutic peptides before their synthesis is crucial for saving time and cost of production. The ToxinPred webserver was used for predicting the toxicity of exemplary peptides. TABLE 6 represents physicochemical properties of exemplary peptides including toxicity, charge, grand average hydropathicity (GRAVY), and instability index.

TABLE 6

Physicochemical properties of exemplary peptides

| Name | Toxicity | Charge | GRAVY | Instability Index |
|---|---|---|---|---|
| Pep-1 | Non-Toxin | 3 | −1.405 | 25.64 |
| Pep-2 | Non-Toxin | 4 | −1.024 | 28.92 |
| Pep-3 | Non-Toxin | 2 | −1.489 | 21.95 |
| Pep-4 | Non-Toxin | 2 | 0.003 | 9.45 |

Referring to TABLE 6, the GRAVY value was calculated by adding the hydropathy value for each residue and dividing by the length of the sequence. Positive values indicated hydrophobicity of the sequence, while negative values indicated the hydrophilic level of the peptide. The instability index provided an estimate of the stability of protein. While instability indexes of all exemplary peptides were below 40, all exemplary peptides were predicted as stable peptides. After designing and conducting in-silico analysis, exemplary peptides of SEQ ID NOs:1-4 were synthesized with high purity of about 90% for conducting laboratory experiments.

Example 4: Determination of the Secondary Structure of Exemplary Peptides

In this example, the stability of exemplary peptides' structures was confirmed by performing the secondary structure's computational prediction through circular dichroism (CD) spectroscopy of exemplary peptides. The CD spectroscopy may be used for determining a secondary structure of exemplary peptides by detecting the difference between the absorption of left-sided polarized light (L-CPL) and the right-sided polarized light (R-CPL) in the far-UV region. The difference occurs when a molecule contains one or more asymmetric light absorption groups. At these wavelengths, the chromophore is the peptide bond, and the signal arises when it is located in a regular, folded environment; as a result, alpha-helix, beta-sheet, and random coil structures give rise to a characteristic shape and magnitude in the CD spectrum.

The CD spectra were recorded in the far-UV spectral region at wavelengths between 190 nm and 250 nm. Technically, a sample solution of each exemplary peptide was prepared at a concentration of about 0.2 mg/mL and transferred to an absorption cuvette with a path length of about 1 mm. The spectrum of the CD pure buffer solution was subtracted from the sample spectrum for the background correction. The results were expressed as molar ellipticity $[\theta]$ (deg cm$^2$ dmol$^{-1}$). Noise in the data was smoothed using the JASCO J-715 software, including the fast Fourier-transform noise reduction routine, which enhances most noisy spectra without distorting their peak shapes. There are many different methods to analyze CD spectra to estimate a secondary structure. One of the most commonly used is K2D, which gives a reasonable estimate of both proteins and polypeptides' helical and sheet contents.

Figure 6A:
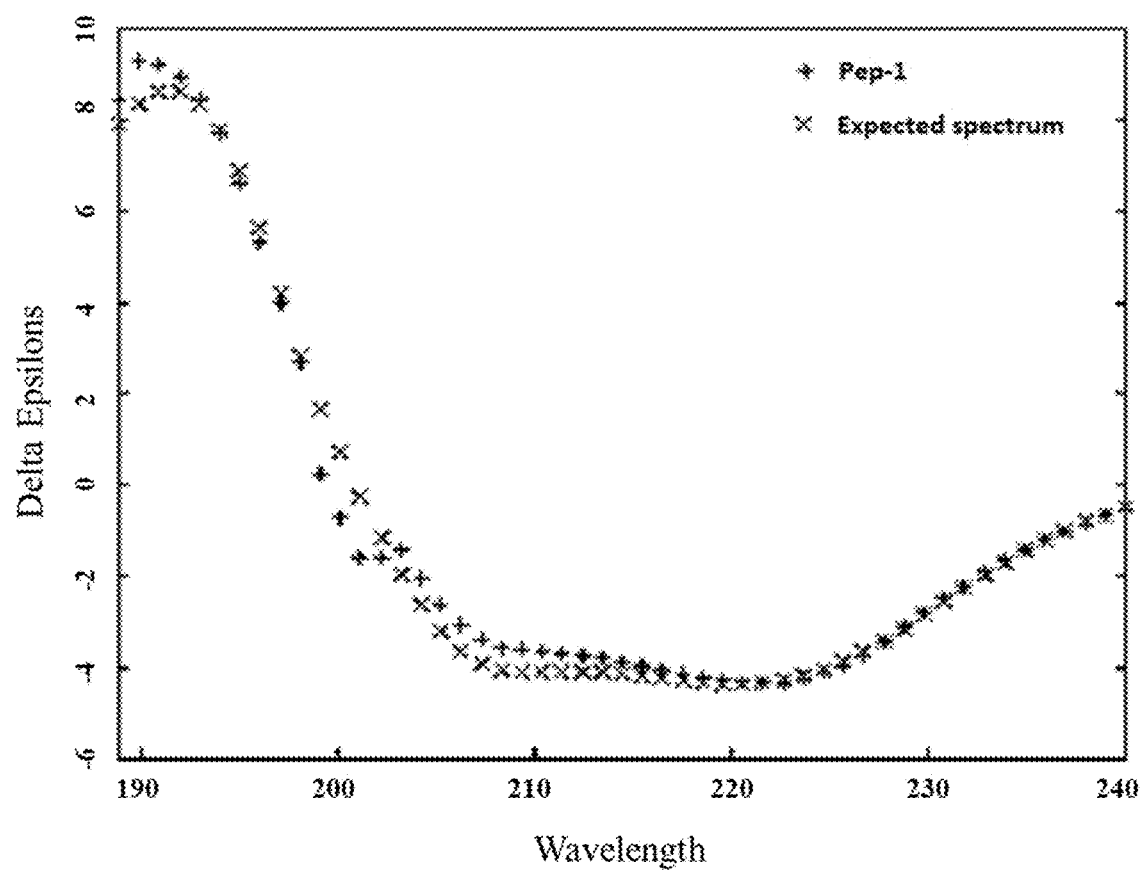
FIG. 6A illustrates the circular dichroism (CD) spectrum of Pep-1 (SEQ ID NO: 1), consistent with one or more exemplary embodiments of the present disclosure.
Figure 6B:
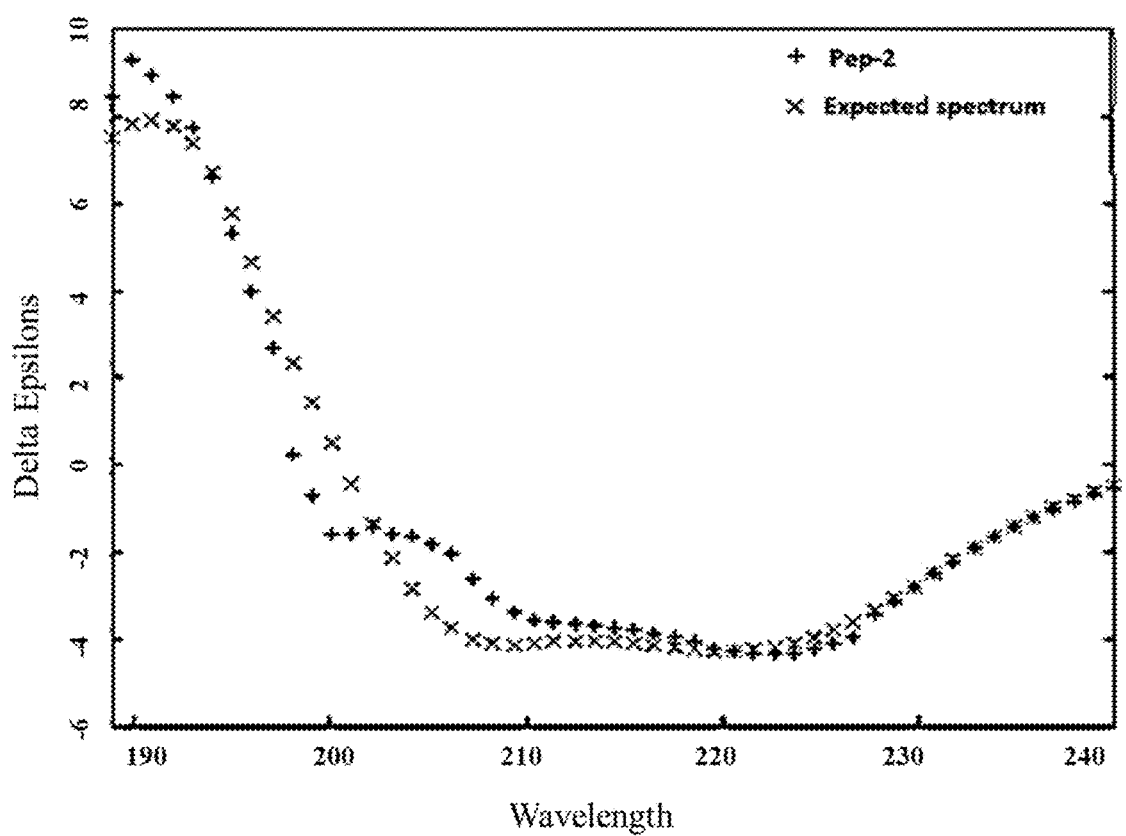
FIG. 6B illustrates the CD spectrum of Pep-2 (SEQ ID NO: 2), consistent with one or more exemplary embodiments of the present disclosure.
Figure 6C:
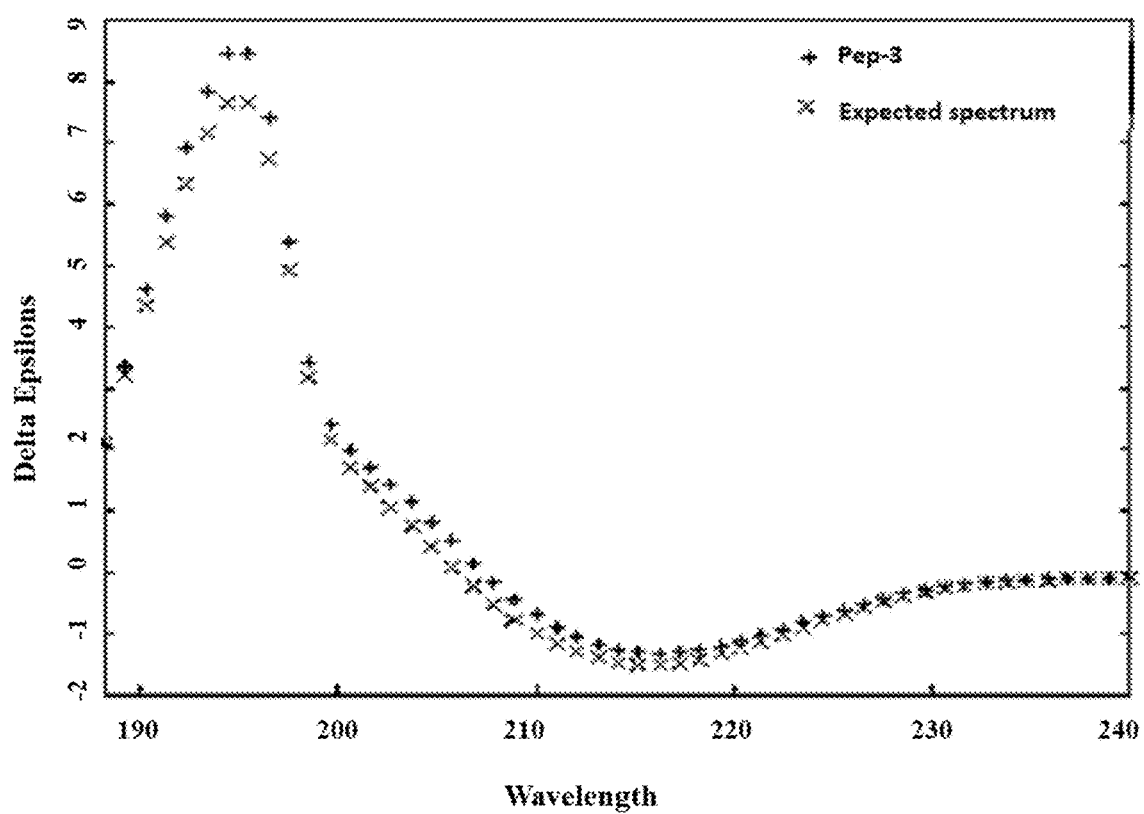
FIG. 6C illustrates the CD spectrum of Pep-3 (SEQ ID NO: 3), consistent with one or more exemplary embodiments of the present disclosure.
Figure 6D:
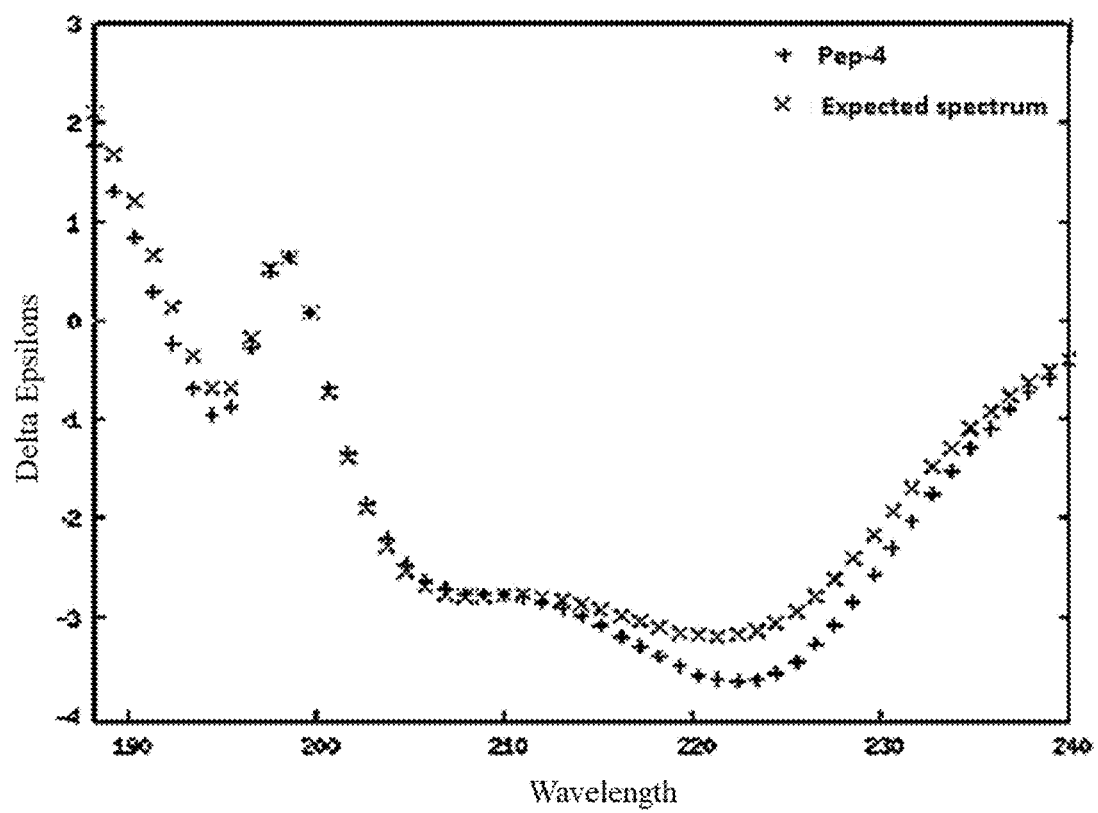
FIG. 6D illustrates the CD spectrum of Pep-4 (SEQ ID NO: 4), consistent with one or more exemplary embodiments of the present disclosure.
Figure 6E:
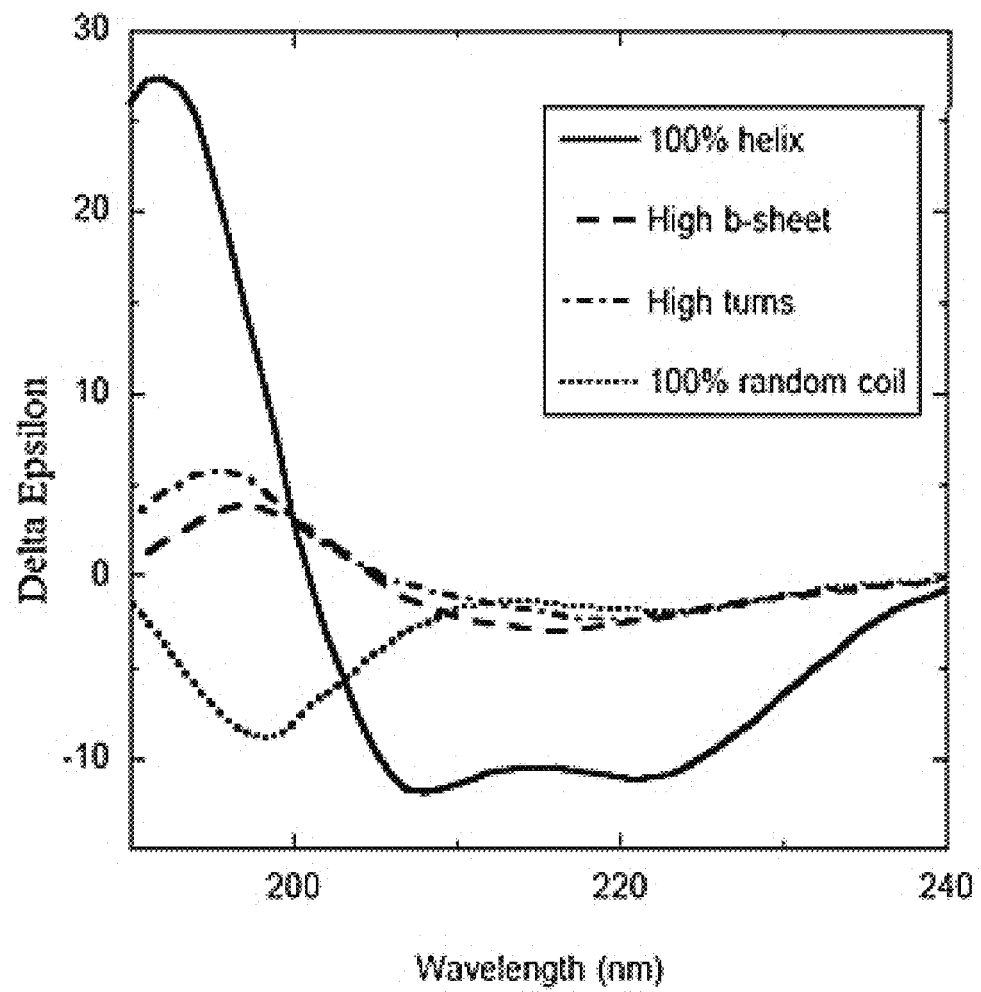
FIG. 6E illustrates the CD spectra of various secondary structures of proteins, consistent with one or more exemplary embodiments of the present disclosure.

FIG. 6A illustrates the CD spectrum of Pep-1 (SEQ ID NO: 1), consistent with one or more exemplary embodiments of the present disclosure. FIG. 6B illustrates the CD spectrum of Pep-2 (SEQ ID NO: 2), consistent with one or more exemplary embodiments of the present disclosure. FIG. 6C illustrates the CD spectrum of Pep-3 (SEQ ID NO: 3), consistent with one or more exemplary embodiments of the present disclosure. FIG. 6D illustrates the CD spectrum of Pep-4 (SEQ ID NO: 4), consistent with one or more exemplary embodiments of the present disclosure. FIG. 6E illustrates the CD spectra of various secondary structures of proteins, consistent with one or more exemplary embodiments of the present disclosure. The expected spectrum in FIGS. 6A-6E, provides an estimate of the maximum total error of the prediction compared with the given input. TABLE 7 represents MD simulation results in the DSSP program, and the CD spectroscopy results for predicting the secondary structure of exemplary peptides.

TABLE 7

Percentage of each secondary structures in peptides

| Peptide Name | Structure element | α-helix | β-sheet | Bend | Turn | Random coil |
|---|---|---|---|---|---|---|
| Pep-1 | MD simulation (DSSP) | 48 | 0 | 19 | 23.5 | 9.5 |
| | CD spectrum | 41 | 7 | 21 | 15 | 16 |
| Pep-2 | MD simulation (DSSP) | 48 | 0 | 15 | 22 | 15 |
| | CD spectrum | 36.5 | 24 | 10 | 15 | 13.5 |
| Pep-3 | MD simulation (DSSP) | 0 | 50 | 25 | 0 | 25 |
| | CD spectrum | 2 | 43 | 20 | 0 | 35 |
| Pep-4 | MD simulation (DSSP) | 0 | 46 | 15 | 19 | 20 |
| | CD spectrum | 14 | 38 | 10 | 15 | 23 |

Referring to TABLE 7 and FIGS. 6A-6E, prediction of the DSSP program for pep-1 is mainly an alpha-helix structure consistent with CD results. While a high percentage of the secondary structure for Pep-2 was predicted as the alpha helix, CD results have shown a lower percent alpha-helix and 24% beta-sheet structure. The predicted structure of DSSP for pep-3 was beta-sheets, and CD results indicated mainly the presence of beta-sheets in this peptide structure. The pep-4 was cyclic via the formation of a disulfide bond. Both the DSSP predictive results and CD results revealed the presence of beta-sheets in its structure.

Example 5: Binding Kinetics of Exemplary Peptides to LRP6

In this example, the binding affinity of exemplary peptides to the LRP6 receptor was determined by performing localized surface plasmon resonance (LSPR) spectroscopy. In the LSPR spectroscopy, the response of free electrons to nanoparticles in the presence of biomolecules may be observed as changes in wavelength and intensity of absorption. A stabilized compound on the nanoparticles' surface is called a ligand, and a second free compound is called an analyte. In this experiment, DKK1, pep-1, pep-2, pep-3, and pep-4 ligands were considered ligands because of their positive surface charge. Also, the LRP6 was used as the analyte because of its negative surface charge. By adding the LRP6 as the analyte in the concentration ranges of $10^{-9}$ M to $10^{-6}$ M, the wavelength changes (plasmon shift) were recorded for each concentration. In the end, the $K_D$ values of exemplary peptides were determined by calculating the sigmoid curve of wavelength changes in terms of LRP6 concentration.

Figure 7:
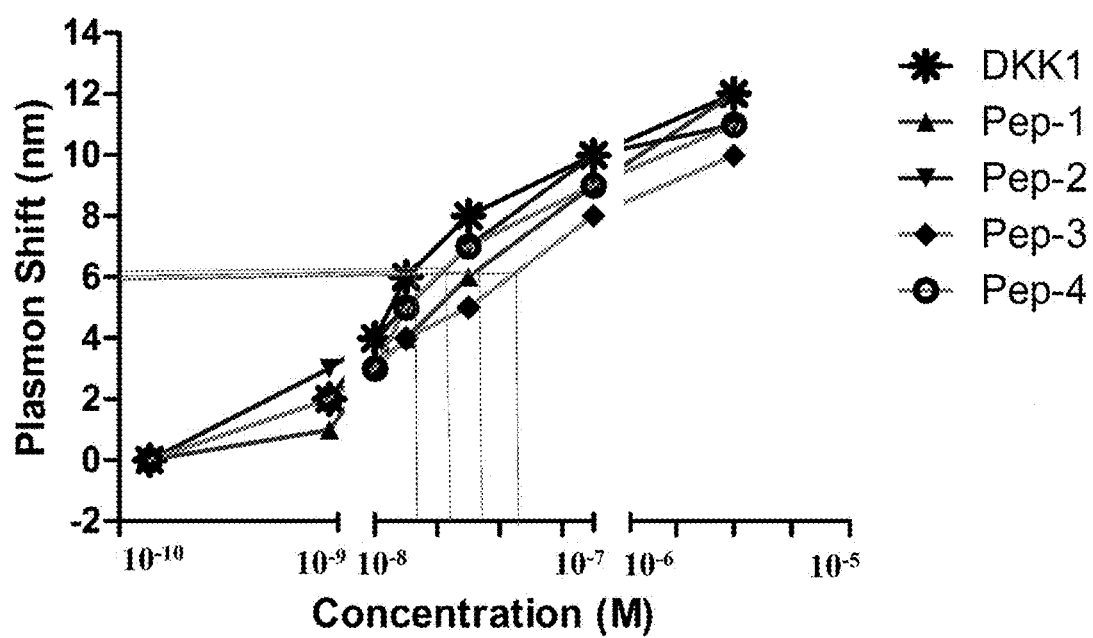
FIG. 7 illustrates a sigmoidal curve of the binding affinity of Dickkopf-1 (DKK1), pep-1 (SEQ ID NO: 1), pep-2 (SEQ ID NO: 2), pep-3 (SEQ ID NO: 3), and pep-4 (SEQ ID NO: 4) at different concentrations to the LRP6, consistent with one or more exemplary embodiments of the present disclosure.

FIG. 7 illustrates a sigmoidal curve of the binding affinity of Dickkopf-1 (DKK1), pep-1 (SEQ ID NO: 1), pep-2 (SEQ ID NO: 2), pep-3 (SEQ ID NO: 3), and pep-4 (SEQ ID NO: 4) at different concentrations to the LRP6, consistent with one or more exemplary embodiments of the present disclosure. Referring to FIG. 7, the analysis of the results of absorption spectra recorded in the curve showed that $K_D$ for DKK1 was about $2.5 \times 10^{-8}$ M and $K_D$ for pep-1, pep-2, pep-3, and pep-4 were about $5.4 \times 10^{-7}$ M, about $4.7 \times 10^{-7}$ M, about $6.2 \times 10^{-7}$ M, and about $5.5 \times 10^{-7}$ M, respectively. As a result, it may be said that after DKK1, pep-2 and pep-4 have a stronger interaction with the LRP6 receptor than pep-1 and pep-3.

Example 6: Effect of Exemplary Peptides on Cell Proliferation

In this example, cytotoxicity effects of exemplary peptides were evaluated by conducting a 3-(4, 5-dimethylthiazol-2-yl)-2, 5-diphenyltetrazolium bromide (MTT) assay on human umbilical vein endothelial cell line (HUVEC), human colorectal adenocarcinoma cell line (SW480), and human colon cancer cell line (HCT116). After cell culture, each cell line was treated with each exemplary peptide at different concentrations between about 100 μM to about 5 mM for different periods between 12 hours and 96 hours. After each treatment, each group's optical density was measured at a wavelength of about 570 nm (with a reference wavelength of 650 nm), and cell viability was compared to the control cells of each category. All experiments were repeated 3 times, and the average values were calculated.

Figure 8A:
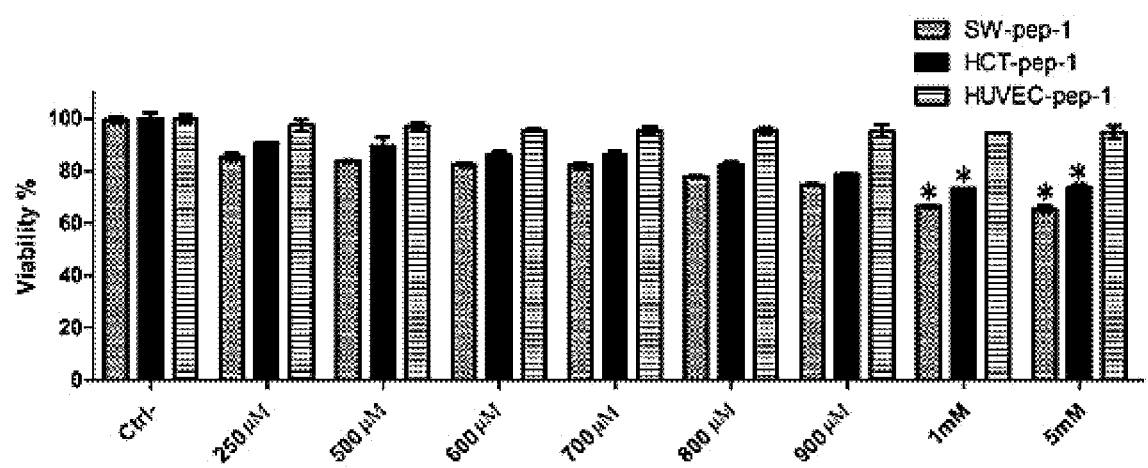
FIG. 8A illustrates the cell viability of SW480, HCT116, and HUVEC cells after 48 hours of treatment with different concentrations of exemplary peptide Pep-1 (SEQ ID NO: 1), consistent with one or more exemplary embodiments of the present disclosure.
Figure 8B:
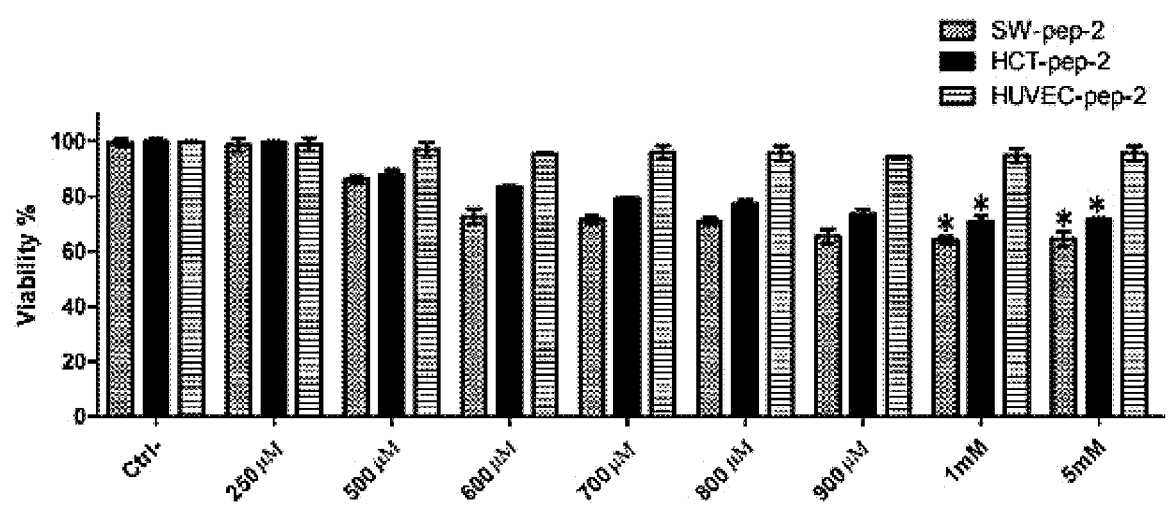
FIG. 8B illustrates the cell viability of SW480, HCT116, and HUVEC cells after 48 hours of treatment with different concentrations of exemplary peptide Pep-2 (SEQ ID NO: 2), consistent with one or more exemplary embodiments of the present disclosure.

FIG. 8A illustrates the cell viability of SW480, HCT116, and HUVEC cells after 48 hours of treatment with different concentrations of exemplary peptide Pep-1 (SEQ ID NO: 1), consistent with one or more exemplary embodiments of the present disclosure. FIG. 8B illustrates the cell viability of SW480, HCT116, and HUVEC cells after 48 hours of treatment with different concentrations of exemplary peptide Pep-2 (SEQ ID NO: 2), consistent with one or more exemplary embodiments of the present disclosure.

Figure 8C:
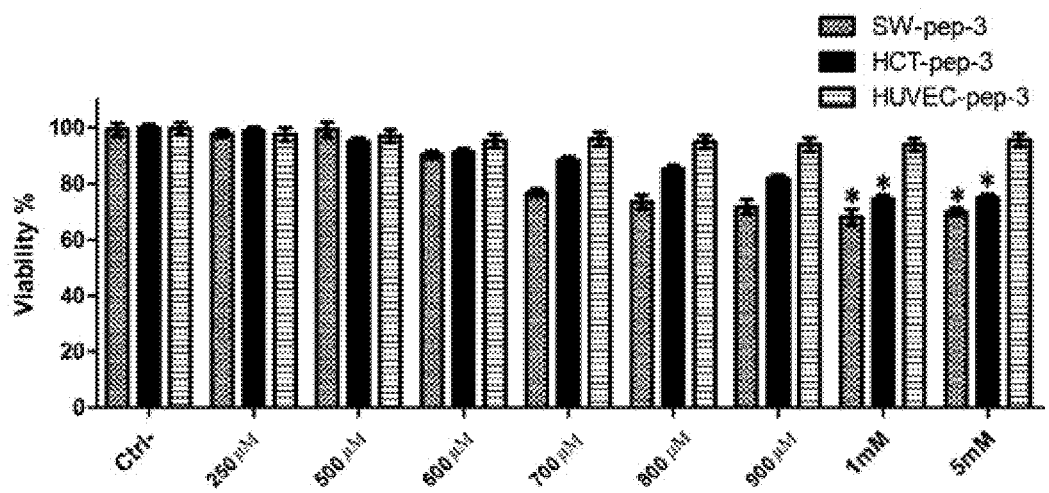
FIG. 8C illustrates the cell viability of SW480, HCT116, and HUVEC cells after 48 hours of treatment with different concentrations of exemplary peptide Pep-3 (SEQ ID NO: 3), consistent with one or more exemplary embodiments of the present disclosure.
Figure 8D:
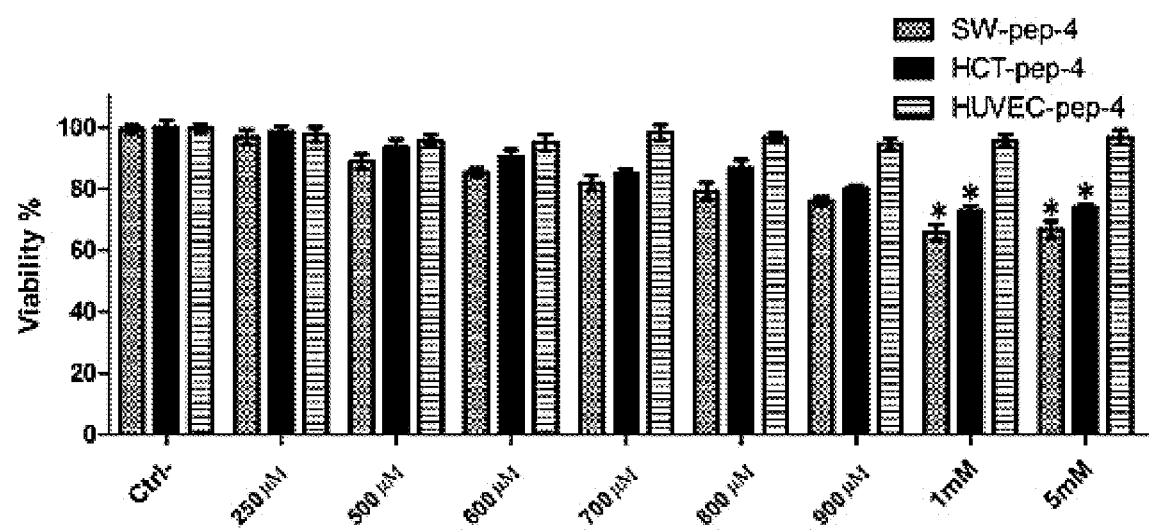
FIG. 8D illustrates the cell viability of SW480, HCT116, and HUVEC cells after 48 hours of treatment with different concentrations of exemplary peptide Pep-4 (SEQ ID NO: 4), consistent with one or more exemplary embodiments of the present disclosure.

FIG. 8C illustrates the cell viability of SW480, HCT116, and HUVEC cells after 48 hours of treatment with different concentrations of exemplary peptide Pep-3 (SEQ ID NO: 3), consistent with one or more exemplary embodiments of the present disclosure. FIG. 8D illustrates the cell viability of SW480, HCT116, and HUVEC cells after 48 hours of treatment with different concentrations of exemplary peptide Pep-4 (SEQ ID NO: 4), consistent with one or more exemplary embodiments of the present disclosure. Referring to FIGS. 8A-8D, treatment with about 1 mM of each exemplary peptide for a time period of about 48 hours was considered as a lethal dose of exemplary peptides for cells SW480, HCT116 cell lines. The rate of decrease in cell proliferation and viability in SW480, HCT116, and HUVEC cells after treatment with 1 mM of exemplary peptides for a time period of about 48 hours, compared to untreated cells, was significant for SW480 and HCT116 cell lines, but this was not significant for HUVEC cell line. As a result, MTT results indicate treatment with exemplary peptides decreased the proliferation and viabilities of cancer cells (SW480 and HCT116 cell lines), while it does not affect these parameters in normal cells (HUVEC cell line).

Example 7: Apoptotic Effect of Exemplary Peptides on Cancer Cells

In this example, the apoptotic effect of exemplary peptides on cancer cells was examined by analyzing the number of apoptotic cells in HCT116 and SW480 and HUVEC cell lines before and after treatment with 1 mM of each exemplary peptide for 24 hours. Annexin V and propidium iodide (PI) staining were used to evaluate the apoptosis induced by treatment with exemplary peptides in each cell line. Stained cells may be counted by flow cytometry to calculate the percentage of apoptosis (Annexin V positive and PI negative) and necrosis percentage (Annexin V positive and PI negative) for each cell line.

Each cell line was also treated with Wnt3a and Wnt5a as positive controls of the Wnt signaling pathway and DKK1 as a natural inhibitor of the Wnt signaling pathway and negative control. The percentage of Annexin V positive and PI negative cells were considered early apoptosis, and the percentage of both Annexin positive and PI-positive cells was considered late apoptosis and necrosis. The sum of these two groups of cells was considered as the cell death rate.

Figure 9A:
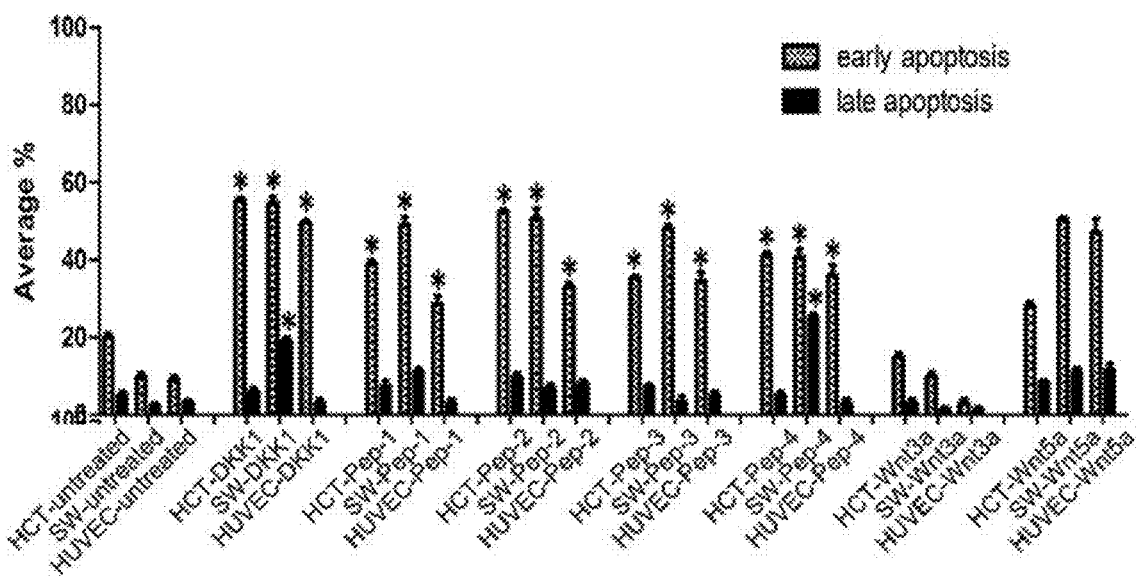
FIG. 9A illustrates percentages of late and early apoptosis in SW480, HCT116, and HUVEC cell lines after treatment with exemplary peptides, DKK1, Wnt3a, and Wnt5a, consistent with one or more exemplary embodiments of the present disclosure.
Figure 9B:
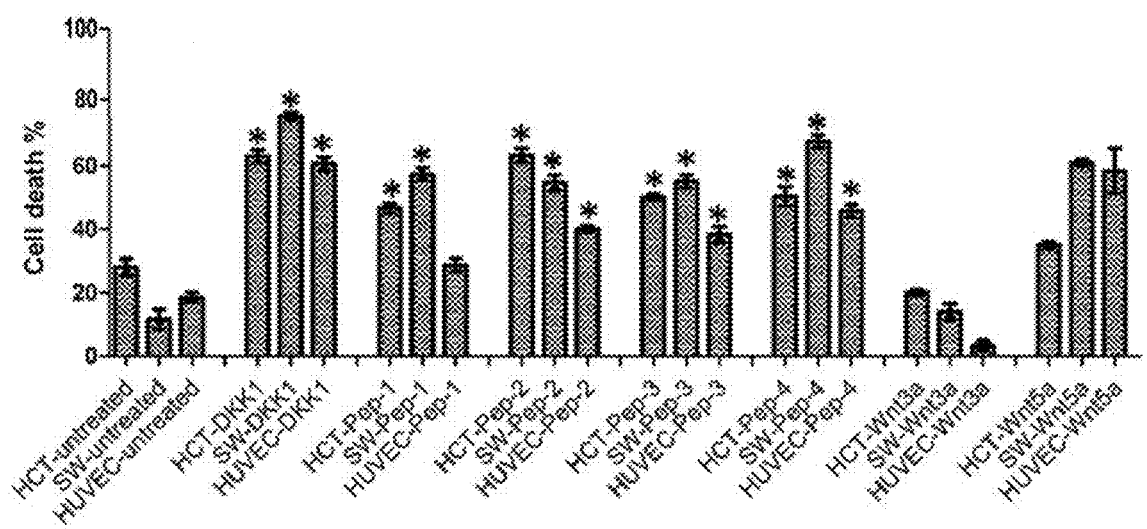
FIG. 9B illustrates percentages of cell death in SW480, HCT116, and HUVEC cell lines after treatment with exemplary peptides, DKK1, Wnt3a, and Wnt5a, consistent with one or more exemplary embodiments of the present disclosure.

FIG. 9A illustrates percentages of late and early apoptosis in SW480, HCT116, and HUVEC cell lines after treatment with exemplary peptides, DKK1, Wnt3a, and Wnt5a, consistent with one or more exemplary embodiments of the present disclosure. FIG. 9B illustrates percentages of cell death in SW480, HCT116, and HUVEC cell lines after treatment with exemplary peptides, DKK1, Wnt3a, and Wnt5a, consistent with one or more exemplary embodiments of the present disclosure. Referring to FIGS. 9A and 9B, apoptosis of SW480 and HCT116 cell lines increased after administering these four peptides. While after treatment with pep-1 and pep-2, in both cancer cell lines, cell death was significantly higher than that of the HUVEC cell line ($p<0.05$), the cell death was significantly higher in SW480 compared with HUVEC after treatment with pep-4 ($p<0.05$). After treatment with pep-1 and pep-4, the cell death of SW480 cell line was significantly higher than that in the HCT116 cell line ($p<0.05$), but in cell line HCT116, the cell death rate induced by pep-2 was significantly higher than that in SW480 ($p<0.05$). As a result, cell death increased more in HCT116 and SW480 cell lines than in the HUVEC cell line after treatment with exemplary peptides.

Example 8: Effect of Exemplary Peptides on Gene Expression

In this example, the effect of exemplary peptides on the expression of LRP6 and downstream genes of the Wnt signaling pathway, such as β-catenin, cyclin D1, and C-MYC, was evaluated at transcription level using real-time PCR and at translation level using Western blotting. The Gapdh gene was used as the reference gene. The expression fold change of more than 2 times (treated cell against untreated cell) was defined as increasing expression, and cases with a fold change of 0.5 to 2 were unchanged, and cases with expression fold change less than 0.5 were considered as a reduction in expression.

Figure 10A:
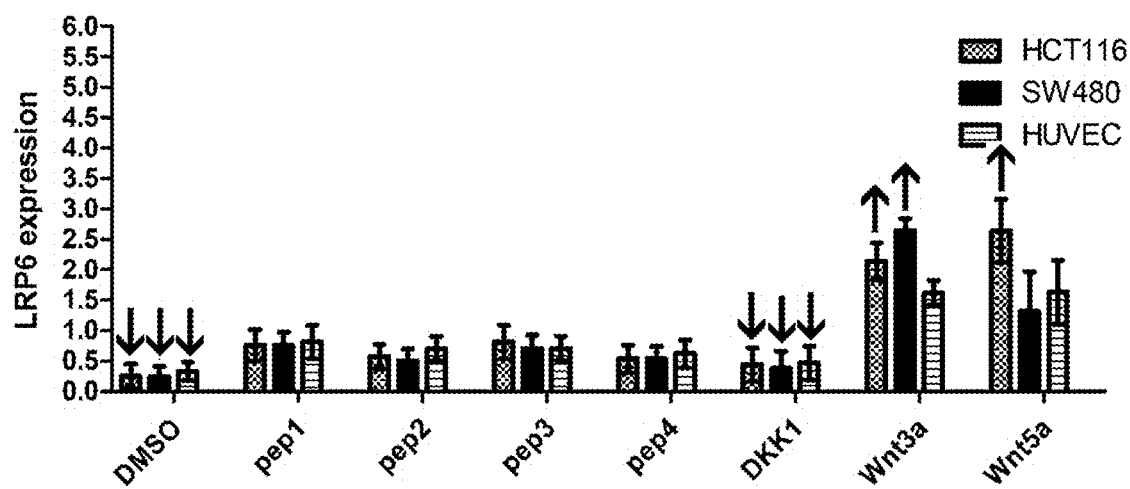
FIG. 10A illustrates the expression of the LRP6 gene in SW480, HCT116, and HUVEC cell lines after treatment with exemplary peptides, consistent with one or more exemplary embodiments of the present disclosure.
Figure 10B:
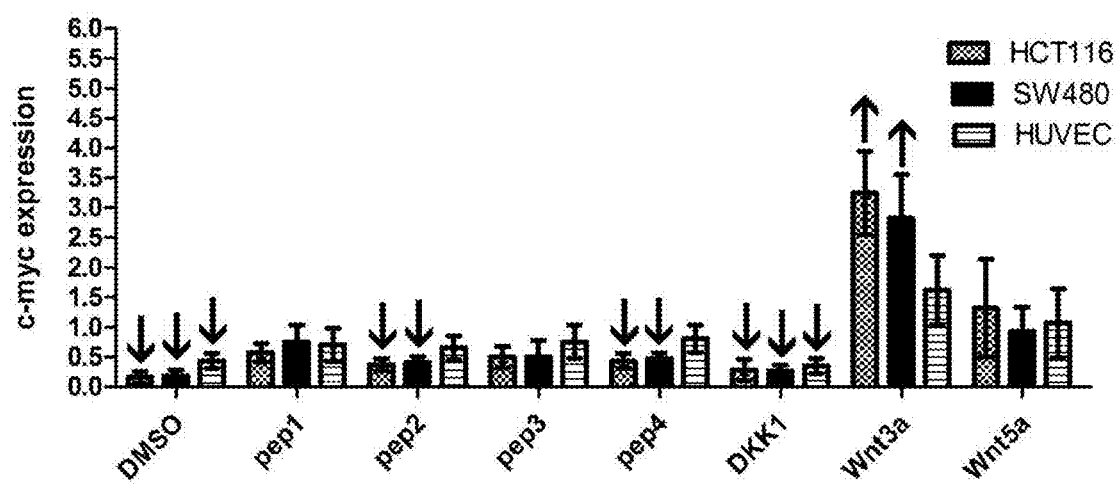
FIG. 10B illustrates the C-MYC gene expression in SW480, HCT116, and HUVEC cell lines after treatment with exemplary peptides, consistent with one or more exemplary embodiments of the present disclosure.
Figure 10C:
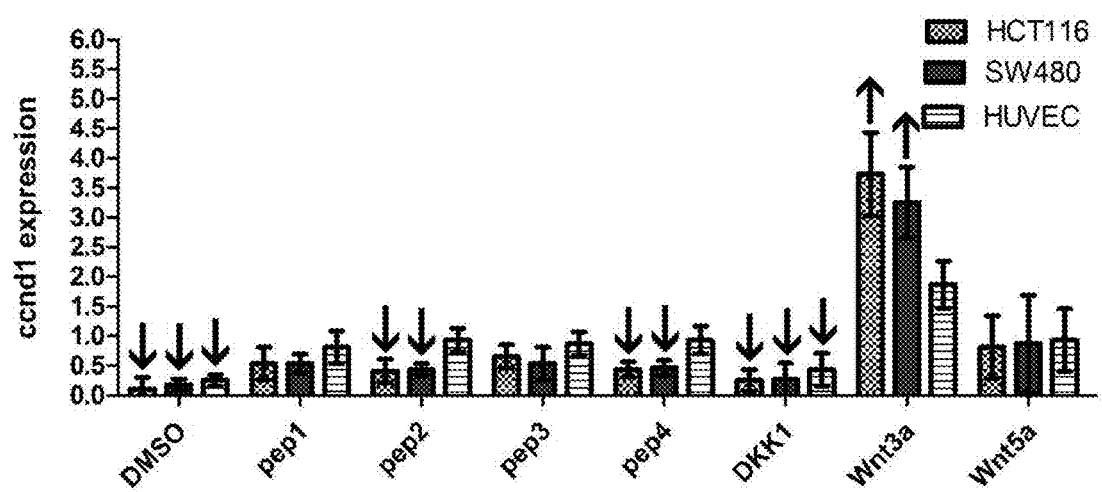
FIG. 10C illustrates the expression cyclin D1 (CCND1) gene in SW480, HCT116, and HUVEC cell lines after treatment with exemplary peptides, consistent with one or more exemplary embodiments of the present disclosure.
Figure 10D:
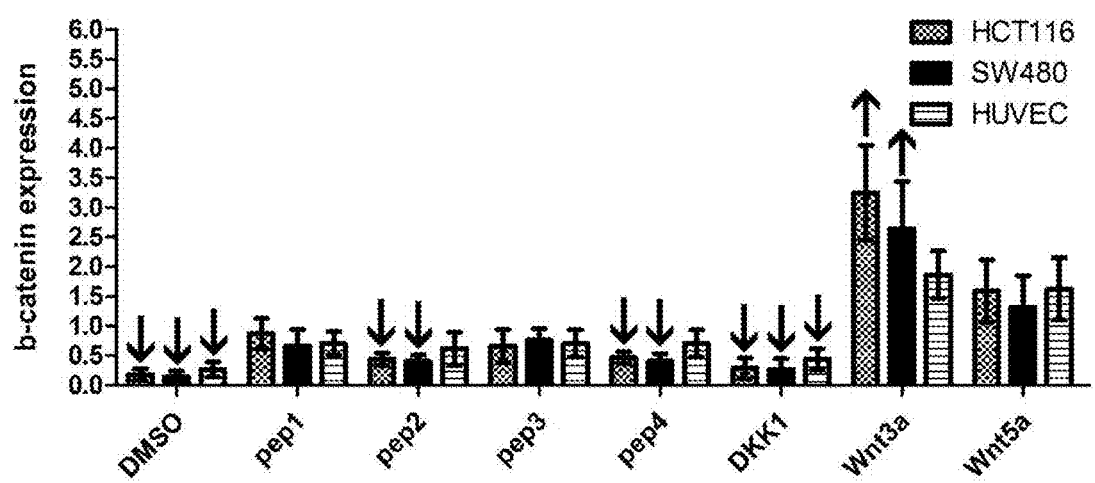
FIG. 10D illustrates the expression β-catenin (CTNBB1) gene in SW480, HCT116, and HUVEC cell lines after treatment with exemplary peptides, consistent with one or more exemplary embodiments of the present disclosure.

FIG. 10A illustrates the expression of the LRP6 gene in SW480, HCT116, and HUVEC cell lines after treatment with exemplary peptides, consistent with one or more exemplary embodiments of the present disclosure. FIG. 10B illustrates C-MYC gene expression in SW480, HCT116, and HUVEC cell lines after treatment with exemplary peptides, consistent with one or more exemplary embodiments of the present disclosure. FIG. 10C illustrates the expression cyclin D1 (CCND1) gene in SW480, HCT116, and HUVEC cell lines after treatment with exemplary peptides, consistent with one or more exemplary embodiments of the present disclosure. FIG. 10D illustrates the expression β-catenin (CTNBB1) gene in SW480, HCT116, and HUVEC cell lines after treatment with exemplary peptides, consistent with one or more exemplary embodiments of the present disclosure.

Referring to FIGS. 10A-10D, treatment with pep-1 and pep-3 did not change the expression of cyclin D1, β-catenin, C-MYC, and LRP-6 in three cell lines. Treatment with pep-2 reduced the relative expression of cyclin D1, C-MYC, and β-catenin in the SW480 and HCT116 cells, but the relative expression of LRP6 in these cells did not change. After treating the HUVEC cell line with pep-2, cyclin D1, β-catenin, C-MYC, and LRP-6 did not change. Treatment with pep-4 reduced expression of cyclin D1, β-catenin, and C-MYC in the SW480 and HCT116. However, the relative level of LRP6 did not change. After treating the HUVEC cell line with pep-4, cyclin D1, β-catenin, C-MYC, and LRP6 genes have not changed. As expected, the Wnt3a protein activates the Wnt signaling pathway by increasing the expression of cyclin D1, β-catenin, C-MYC, and LRP6 in SW480 and HCT116, respectively, but the level of these genes in the HUVEC did not change. At the same time, after treatment with Wnt5a, as an effective ligand for non-canonical Wnt signaling pathway, the relative expression level of cyclin D1, β-catenin and C-MYC and LRP6 genes in three cell lines did not change. Also, treatment with DKK1 reduced the relative expression of downstream genes in all cell lines.

Figure 11A:
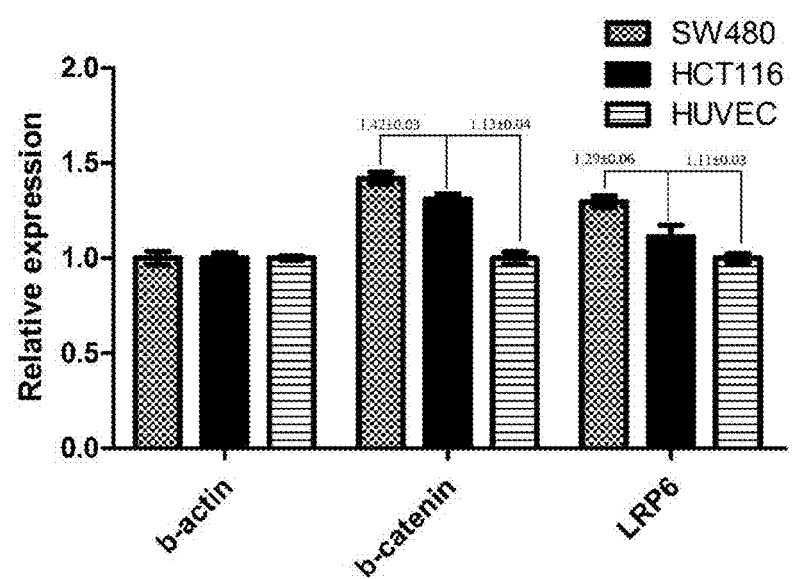
FIG. 11A illustrates relative expression β-actin, β-catenin, and LRP6 in SW480, HCT116, and HUVEC cell lines, consistent with one or more exemplary embodiments of the present disclosure.

Also, the effect of exemplary peptides on the levels of LRP6 and β-catenin proteins in the β-catenin/Wnt signaling pathway was investigated by Western blotting. Also, each protein's relative expression was determined through signal densitometry of each Western blot band. FIG. 11A illustrates relative expression β-actin, β-catenin, and LRP6 in SW480, HCT116, and HUVEC cell lines, consistent with one or more exemplary embodiments of the present disclosure. Referring to FIG. 11A, the relative expressions of β-catenin and LRP6 in SW480 and HCT116 were higher than HUVEC as a normal cell. These results may be due to increased activation of the Wnt signaling pathway in SW480 and HCT116 cells as cancerous cell lines.

Figure 11B:
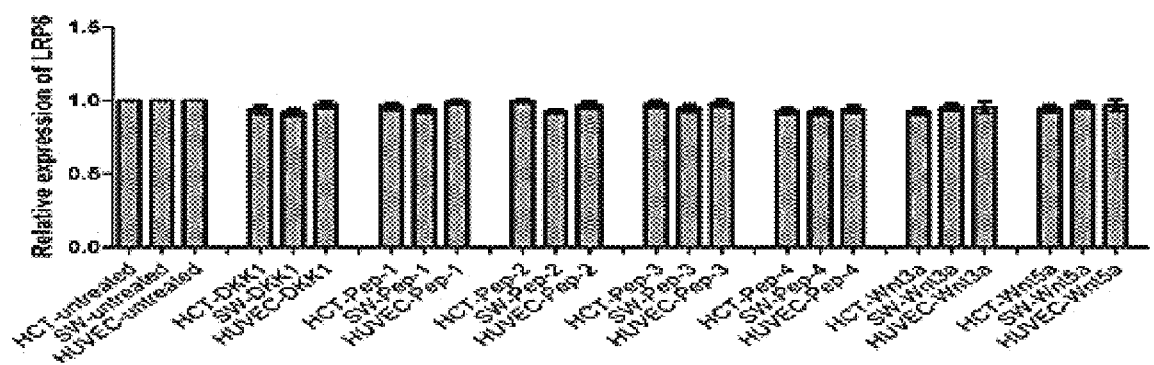
FIG. 11B illustrates the relative expression of LRP6 protein in SW480, HCT116, and HUVEC cell lines after treatment with exemplary peptides, consistent with one or more exemplary embodiments of the present disclosure.

FIG. 11B illustrates the relative expression of LRP6 protein in SW480, HCT116, and HUVEC cell lines after treatment with exemplary peptides, consistent with one or more exemplary embodiments of the present disclosure. Referring to FIG. 11B, the results showed that treatment with each of exemplary peptides had no significant effect on the level of LRP6. Also, the results of this study showed that treatment with DKK1 did not alter LRP6 expression in SW480, HCT116, and HUVEC cell lines.

Figure 11C:
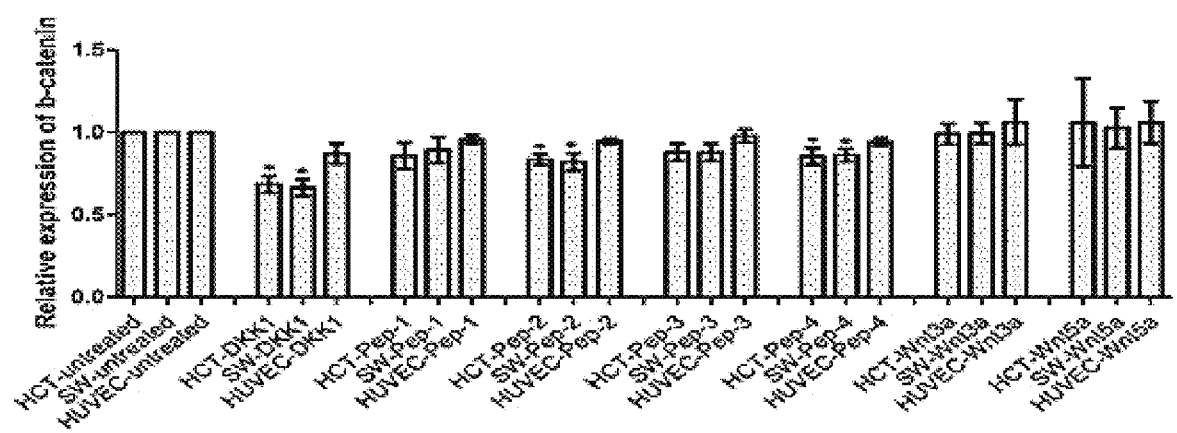
FIG. 11C illustrates the relative expression of the β-catenin protein in SW480, HCT116, and HUVEC cell lines after treatment with exemplary peptides, consistent with one or more exemplary embodiments of the present disclosure.

FIG. 11C illustrates the relative expression of the β-catenin protein in SW480, HCT116, and HUVEC cell lines after treatment with exemplary peptides, consistent with one or more exemplary embodiments of the present disclosure. Referring to FIG. 11C, signal densitometry analysis of bands in DKK1-treated cells showed that β-catenin levels decreased by 40% in both SW480 and HCT116 cell lines. Also, treatment with pep-2 (SEQ ID NO: 2) and pep-4 (SEQ ID NO: 4) had a 20% reduction effect compared to DKK1 on β-catenin in both SW480 and HCT116 cell lines. However, treatment with pep-1 (SEQ ID NO: 1) and pep-3 (SEQ ID NO: 3) had no significant effect on β-catenin protein content.

Example 9: Cell Cycle Analysis after Treatment with Exemplary Peptides

In this example, the effect of exemplary peptides on the cell cycle was determined through flow cytometry and measurement of DNA content in cells. In this experiment, HCT116, SW480, and HUVEC cell lines were cultured in 24-well plates and treated with 1 mM of each exemplary peptide for 24 hours. Each cell line was also treated with Wnt3a and Wnt5a as positive controls of the Wnt signaling pathway and DKK1 as a natural inhibitor of the Wnt signaling pathway and negative control.

Figure 12:
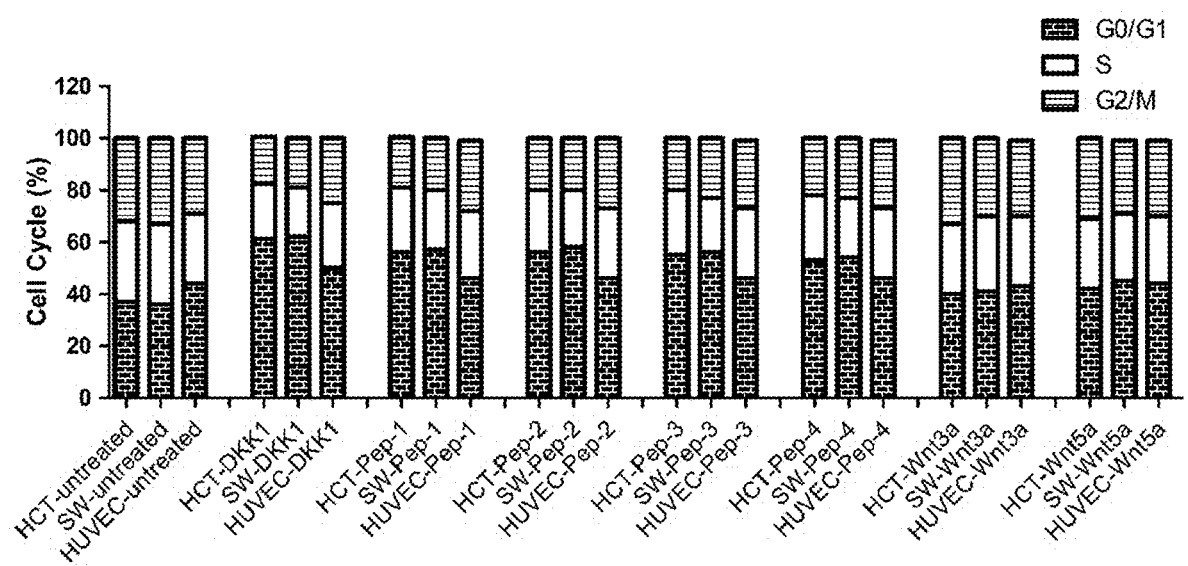
FIG. 12 illustrates the percentage of cells at G0/G1, S, and G2/M stages of the cell cycle in HCT116, SW480, and HUVEC cell lines before and after treating cells with exemplary peptides, consistent with one or more exemplary embodiments of the present disclosure.

FIG. 12 illustrates the percentage of cells at G0/G1, S, and G2/M stages of the cell cycle in HCT116, SW480, and HUVEC cell lines before and after treatments with exemplary peptides, consistent with one or more exemplary embodiments of the present disclosure. Referring to FIG. 12, the S and G2/M stage percentage decreased in all cell lines, especially HCT116 and SW480, after treatment with exemplary peptides and DKK1. In contrast, the percentage of cells in the G0/G1 stage was increased. In HCT116 and SW480 cell lines, the percentage of cells in the G0/G1 stage increased by an average of 10% to 20% after treatments. These data indicate that treatment with exemplary peptides and DKK1 inhibits their proliferation by delaying the cell cycle in the G0/G1 phase and increasing the number of cells at this stage. Also, a reduced percentage of cells in G2 and S stages may be due to exemplary peptides' anti-proliferative properties. The treatment with Wnt3a ligand has led the cells to the cell division stage, with a higher percentage of HCT116, SW480, and HUVEC cells in the S and G2/M phases.

Overexpression of DKK1 may be associated with the activation of apoptosis in various tumor cell models. The cell proliferation index may be calculated by dividing the percentage of cells present in the S and G2 stages by the percentage of cells in the G1, S, and G2 stages. In all cell lines, the least proliferation index was calculated for all cell lines after DKK1 treatment. Also, the proliferation index in SW480 and HCT116 cell lines decreased after treatment with exemplary peptides (SEQ ID NOs: 1-4). On the other hand, the decrease in the proliferation index of HUVEC cells was smaller than that of SW480 and HCT116 cell lines.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A composition for targeting low-density lipoprotein receptor-related protein 6 (LRP6)-overexpressed cells, the composition comprising a peptide, the peptide comprising SEQ ID NO: 1 and SEQ ID NO: 3.

2. The composition of claim 1 further comprising at least one of SEQ ID NO: 2 and SEQ ID NO: 4.

3. The composition of claim 1 further comprising a tag conjugated to the peptide.

4. The composition of claim 3, wherein the tag comprises at least one of a chemotherapeutic drug, a toxin, an anticancer growth inhibitor compound, an anticancer siRNA, and an anticancer antagomir.

5. The composition of claim 4, wherein the chemotherapeutic drug comprises at least one of cisplatin, paclitaxel, carboplatin, topotecan, 5-fluorouracil, mitomycin C, docetaxel, oxaliplatin, epirubicin, cyclophosphamide, methotrexate, doxorubicin, and irinotecan.

6. The composition of claim 3, wherein the tag comprises at least one of a radioactive substance, a dye, a contrast agent, a fluorophore molecule, a nanoparticle, a bioluminescent molecule, an affinity agent, and a magnetic agent.

7. The composition of claim 1, wherein the peptide has a binding affinity to LRP6 with a dissociation constant ($K_d$) between 1 μM and 1000 μM.

8. A method for targeting low-density lipoprotein receptor-related protein 6 (LRP6)-overexpressed cells in a subject, the method comprising administering an effective amount of a composition to the subject, the composition comprising a peptide, the peptide comprising SEQ ID NO: 1 and SEQ ID NO: 3.

9. The method of claim 8, wherein the composition further comprises at least one of SEQ ID NO: 2 and SEQ ID NO: 4.

10. The method of claim 8, wherein the LRP6-overexpressed cells comprise LRP6-overexpressed cells of at least one of colorectal cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, and bladder cancer.

11. The method of claim 8, wherein the composition further comprises a tag conjugated to the peptide.

12. The method of claim 8, wherein the subject comprises at least one of a human and an animal.

13. The method of claim 8, wherein administering the effective amount of the composition to the subject comprises at least one of intravenous, intratumoral, intradermal, intramuscular, subcutaneous, rectal, and oral administration.

14. The method of claim 8 further comprising killing the LRP6-overexpressed cells in the subject by conducting at least one of magnetic hyperthermia, photodynamic therapy, and photothermal therapy.

15. A method for detecting low-density lipoprotein receptor-related protein 6 (LRP6)-overexpressed cells in a biological sample, the method comprising:
  putting the biological sample in contact with a composition, the composition comprising:
    a peptide comprising SEQ ID NO: 1 and SEQ ID NO: 3; and
    a tag conjugated to the peptide; and
  determining the presence of an LRP6-overexpressed cell in the biological sample responsive to detecting the peptide bound to the LRP6-overexpressed cell.

16. The method of claim 15, wherein the composition further comprises at least one of SEQ ID NO: 2 and SEQ ID NO: 4.

17. The method of claim 15, wherein detecting the peptide bound to the LRP6-overexpressed cell comprises detecting the peptide bound to the LRP6-overexpressed cell by conducting at least one of a chemiluminescent assay, an immunofluorescent assay, enzyme-linked immunosorbent assay (ELISA), radioimmunoassay, a Western blot assay, an enzyme immunoassay, an immunoprecipitation assay, an immunohistochemical assay, an immunochromatographic assay, a dot blot assay, a slot blot assay, confocal imaging, laser scanning microscopy, and flow cytometry.

18. The method of claim 15, wherein putting the biological sample in contact with the composition comprises putting at least one of a blood sample, a plasma sample, a serum sample, a urine sample, a fecal sample, a cervix sample, and a semen sample in contact with the composition.

* * * * *